Figure 2:
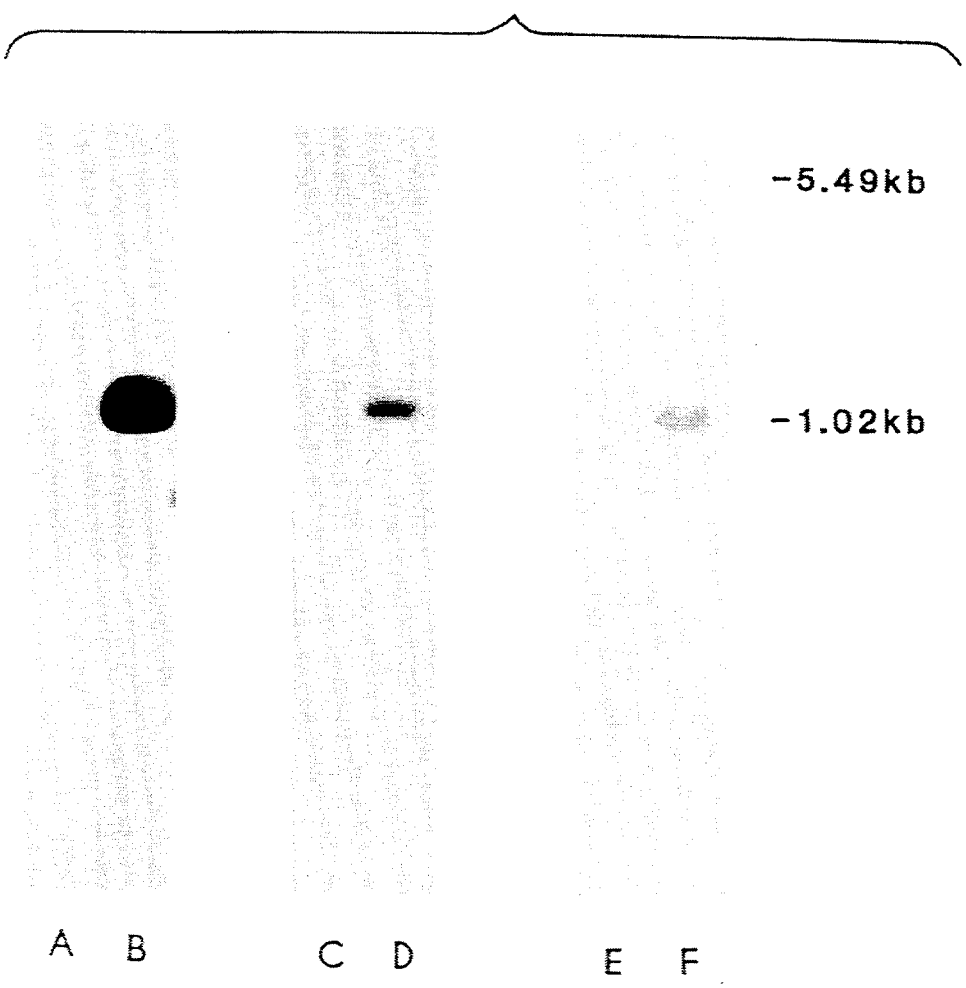

United States Patent [19]

McKenzie et al.

[11] Patent Number: 5,451,669
[45] Date of Patent: Sep. 19, 1995

[54] DNA ENCODING FOR AN FC RECEPTOR FOR IMMUNOGLOBULIN

[75] Inventors: Ian F. C. McKenzie, Brunswick; Mark P. Hogarth, West Footscray; Margaret L. Hibbs, Nunawading; Bernadette M. Scott, Edithvale; Lisa Bonadonna, Elsternwick, all of Australia

[73] Assignee: The University of Melbourne, Victoria, Australia

[21] Appl. No.: 896,457

[22] Filed: May 27, 1992

Related U.S. Application Data

[63] Continuation of Ser. No. 174,991, Mar. 1, 1988, abandoned.

[30] Foreign Application Priority Data

May 29, 1986 [AU] Australia ............... PH6166

[51] Int. Cl.⁶ ............. C07H 15/12; C12N 1/22; C12P 21/06
[52] U.S. Cl. ............. 536/23.5; 435/69.1; 435/252.3; 435/320.1; 530/388.22
[58] Field of Search ........... 536/23.5; 435/91, 69.1, 435/252.3, 252.33, 320.1; 530/388.22

[56] References Cited

U.S. PATENT DOCUMENTS 4,948,874  8/1990  Kronvall et al. .............. 530/350
4,962,035  10/1990 Leder et al. .................. 435/320

OTHER PUBLICATIONS

Vaughn et al J. Immunol. 135(6) 4059–65 (1985).
Toh et al. *Nature* 318: 388–389 (1985).
Lowy et al. *Proc. Natl Acad Sci. USA* 80: 2323–27 (1983).
Martens et al *Proc. natl Acad Sci USA* 82: 2460–4 (1985).
Liu et al. *Proc. Natl Acad Sci USA* 82: 4100–4104 (1985).
Hibbs et al. *Immunogenetics* 22: 335–348 (1985).
Hibbs et al. *Proc. Natl Acad. Sci. USA* 83: 6980–6984 (1986).
Vaughn, et al. *J. of Immunology* 135(6): 4059–65 (1985).
Suggs et al *Proc Natl Acad Sci USA* 78(11): 6613–17 (1981).
Creighton, *Proteins: Structures & Molecular Properties* (Freeman & Co. 1984) pp. 39–42.
Loube et al., "Isolation of an Fc–Binding Protein from the Cell Membrane of a Macrophage-Like Cell Line (P388D) After Detergent Solubilization," *J. Immunol.*, 120(3): 709–715 (1978).
Anderson et al., "Characterization of the Fc Receptor for IgG on a Human Macrophage Cell Line, U937," *J. Immunol.*, 125(6): 2735–2741 (1980).
Kulczycki et al., "Purificaton of Fc Receptor from Rabbit Alveolar Macrophages That Retains Ligand-Binding Activity", *J. Immunol.*, 124(6): 2772–2779 (1980).

(List continued on next page.)

sitivity: Hay Fever And Asthma", Chapter 21, pp. 579–658.
Henney, Christopher s. and Gillis, Steven, "Cell-Mediated Cytotoxicity", In: *Fundamental Immunodogy*, Chapter 25, pp. 669–684 (1984).

*Primary Examiner*—Garnette D. Draper
*Assistant Examiner*—Shelly Guest Cermak
*Attorney, Agent, or Firm*—Foley & Lardner

[57] ABSTRACT

A receptor for the Fc portion of immunoglobulin, derived from mouse or human cells, the receptor exhibiting the ability to bind to the Fc portion of mouse and human immunoglobulin and comprising a transmembrane proteins having about 280–301 amino acids including two substantially regularly spaced pairs of Cys residues and two or four potential N-linked glycosylation sites. The present invention also provides for a nucleotide sequence, gene, cDNA clone or a vector containing same capable of encoding the above receptor.

2 Claims, 18 Drawing Sheets

OTHER PUBLICATIONS

Hempstead et al., "Characterization of the IgE Receptor Isolated From Human Baseophils," *J. Immunol.* 123(5): 2283–2291 (1979).

Hibbs et al., "The Murine Fc Receptor for Immunoglobulin: Purification, Partial Amino Acid Sequence, and Isolation of cDNA clones," *Proc. Nat'l. Acad. Sci., U.S.A.* 83: 6980–6984 (1986).

Lewis et al., "A Complementary DNA Clone for a Macrophage–Lymphocyte Fc Receptor," *Nature* 324: 372–375 (1986).

Ravetch et al., "Structural Heterogeneity and Functional Domains of Murine immunoglobulin G Fc Receptors," *Science* 234: 718–725 (1986).

Gorini et al., "Analysis of Membrane Glycoproteins Binding To Immunocomplexes," *Biochemical Society Transactions* 14: 74–75 (1986).

Vaughn et al., "Characterization of Human IgG Fc Receptors," *J. Immunol.* 135(6): 4059–4065 (1985).

Dickler, Howard B., "Lymphocyte Receptors For Immunoglobulin", *In: Advances In Immunology* v. 24, pp. 167–215 (1976).

Vernier, Robert L., "Clinical Aspects Of Glomerulonephritis", *In: Immunological Diseases* 2nd Ed., pp. 1134–1149 (1971).

Henson, P. M., "Antibody And Immune-Complex--Mediated Allergic And Inflammatory Reactions", *In: Clinical Aspects Of Immunology*, 4th Ed., pp. 687–709 (1982).

Ishizaka, Kimishige, "Experimental Anaphylaxis", *In: Immunological Diseases* 2nd Ed., pp. 202–219 (1971).

Platts–Mills, T. A. E., "Type I or Immediate Hypersen-

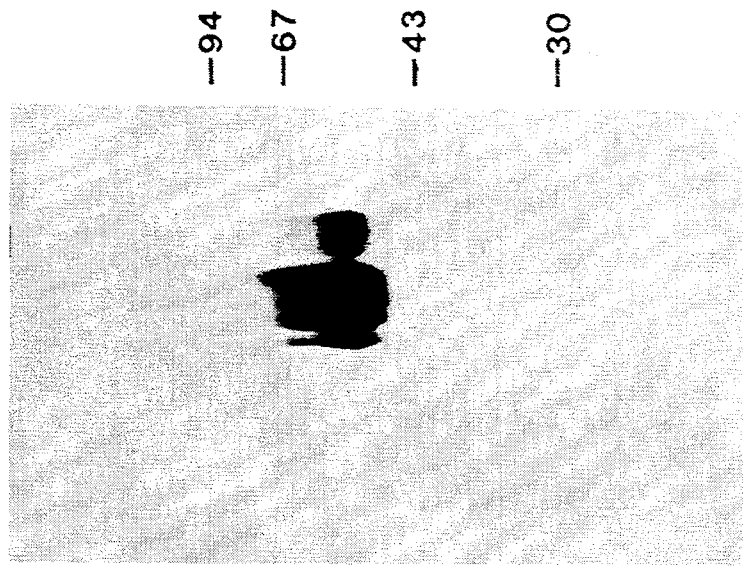
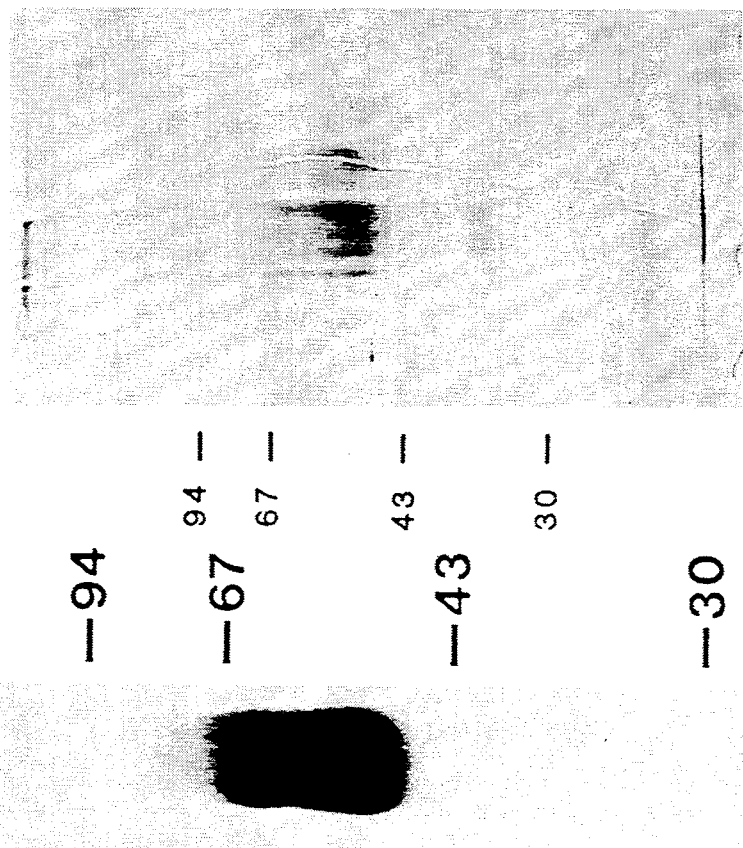
FIG. 1A  FIG. 1B  FIG. 1C

FIG. 3B

```
CTGCAGACTCGCTCCAGAGCTGATGGGAATCCTGCCGTTCCTACTGATCCCC
                                                                                 -29                       -20
                                                              Met Glu Ser Asn Trp Thr Val His Val Phe Ser Arg Thr Leu Cys
                                                              ATG GAG AGC AAC TGG ACT GTC CAT GTG TTC TCA CGG ACT TTG TGC
                                                              -1 +1                                    10
His Met Leu Trp Thr Ala Val Leu Asn Leu Ala Ala Gly Thr His Asp Gly Thr Lys Val Val Lys Leu Glu Pro Pro Trp
CAT ATG CTA TGG ACA GCC GTG CTA AAT CTT GCT GCT GGG ACT CAT GAT CTT GGG ACC AAG GTG GTC AAA CTC GAG CCC CCG TGG
         -10                                           20                             30                             40
Ile Gln Val Leu Lys Glu Asp Thr Val Thr Cys Glu Gly Ser Tyr Thr Phe Ser Thr Ser Gly Asn Pro Gly Glu Gln Trp Phe His Asn
ATC CAG GTG CTC AAG GAA GAC ACG GTG ACA TGC GAA GGG AGC TAC TTT TCT ACC TCT GGG AAC CCT GGG GAG CAG TGG TTC CAC AAT
                               50                                      60                              70
Gly Arg Ser Ile Arg Gln Val Ser Asp Leu Thr Val Ala Val Asn Asp Ser Gly Glu Tyr Arg Cys Gln Met Glu
GGG AGG TCC ATC CGG CAG GTC TCT GAC CTC ACG GTA GCC ACA GTC AAT GAC AGT GGA GAA TAT CGG TGT CAA ATG GAG
                    80                                      90                              100
Gln Thr Arg Leu Ser Asp Pro Val Asp Leu Gly Val Ile Ser Leu Leu Gln Thr Pro Gln Leu Phe Leu Glu Gly
CAG ACC CGC CTC AGC GAC CCT GTA GAT CTG GGA GTG ATT TCT GAC CTG CTC CAG ACC CCT CAG CTG TTT CTG GAA
                                   110                                   120                              130
Glu Thr Ile Thr Leu Arg Cys His Ser Trp Arg Asn Lys Leu Leu Asn His Ser Val Ser Phe Phe Phe Pro Asn His Val Ser Gly Lys Ser Val Arg Thr
GAA ACC ATC ACG CTA AGG TGC CAT AGC TGG AGG AAC AAA CTA CTG AAC CAC AGT GTC AGT TCA TTC TTC TTC CCA AAT CAC GTG AGT GGG AAA TCC GTG AGG ACA
                                             140                                     150                              160
His His Tyr Ser Ser Asn Phe Ser Ile Pro Lys Ala Asn His Thr Leu Tyr Cys Lys Gly Ser Leu Gly Arg Thr
CAT CAC TAC AGT AGT AAT TTC TCT ATC CCC AAA GCC AAC CAC ACT CTA TAC TGC AAA GGA AGT CTA GGA AGG ACA
                              170                                   180
Leu His Gln Ser Lys Pro Val Thr Ile Ile Val Gln Gly Pro Lys Ser Ser Arg Tyr Arg Gln Leu Thr Leu Leu Pro Ala Leu Ala Val
CTG CAC CAG TCC AAG CCT GTC ACC ATC ATT GTT CAA GGG CCC AAG TCC AGC AGG TAC AGG CAG CTC ACT CTC CCA GCT CTC GCC GTC
               190                                       200                                   210
Thr Gly Ile Ala Val Ala Ala Ile Val Leu Ile Leu Val Ser Leu Val Tyr Leu Lys Lys Lys Leu Ile Thr Thr Ala Leu Pro Gly Asn
ACT GGG ATT GCT GTC GCA GCC ATT GTT CTA ATT ATC TTA GTC TCC CTT GTA TAC CTT CTC AAG AAA AAG CAG ATT ACA ATT GTG GCT GTC
      220                                      230                                     240
Pro Asp His Arg Glu Met Gly Glu Thr Leu Pro Glu Glu Gly Glu Gly Val Tyr Asn Pro Asp Tyr Gln Pro Ser Val Pro Gly Asn
CCT GAT CAC AGG GAA ATG GGA GAA ACC CTT CCA GAG GAA GTA GGT GAG TAC AAT CCT GAT TAC AAA CAG TCA GTT CCT CCA GGA AAC
               250                                     260                                     270
Gly Pro Pro Ser Gly Leu Glu Pro Thr Ser Ser Ser Pro Tyr Asn Pro Pro Asp Leu Glu Glu Ala Pro Lys Thr Glu Ala Glu Asn
GGG CCT CCA TCT GGA CTG GAG CCG ACA AGC AGC AGC CCA TAC AAT CCT GAT CTG GAA GAA GCT CCC AAA ACT GAG GCT GAG AAC
           280                                      290                                      300
Thr Ile Thr Tyr Ser Leu Leu Lys His Pro Glu Ala Leu Asp His Asp Tyr Gln Asn His Ile ***
ACG ATC ACC TAC TCA CTC CTC AAG CAT CCC GAA GCC TTG GAT CAT GAT TAC CAA AAC CAC ATT TAG TCTCCCTTGGC
ATTGGAAAAGCAAGCCAGGAAAGGCCAGGATCTAGTGTCTCCTGGTCCAAGGATGCTGTAGATATTAAAGAAACATCCAGAGTCACTTCTGTGAGTCCTGAAACCAACAGACA
CTACGAGATTGGTTCCAATGGTTGACTGTACTAATGACTCCATAACTTACAGCTTCCACTACAGCTTCTGCTATCGATCCAGACACACTGCCACTAAAATTAATCAACTTAC
TGCCGTTAAGAGACTGCAG
```

FIG. 4A

PROTEIN    RESIDUE    SEQUENCE
FcR        5-86       PKAVVKLEPPWIQVLKEDTVTLTCEGTHNPGNSSTQWFHN
FcR        88-175     WLLLQTPQLVFLEGETITLRCHSWRNKLLNRISFFHN

```
GRSIR-SQVQASYTF-KATVNDSGEYRCQ--HEQT-RLSDPVDLCVI
EKSVRYHHYSSNFSIPKANHSHSGQYYCKGSLGRTLHQSKPVTITVQCIK
```

FIG. 4B

PROTEIN    RESIDUE    SEQUENCE
FcR        5-46       PKAVVKLEPPWIQVLKEDTVTLTCEGTHNPGNSSTQW
FcR        86-124     ISDWLLLQTPQLVFLEGETITLRCHSWRDKLLNRISF
V1         1-37       QAVVTQESA-LTTSPGETVTLTCRSSTGAVTTSNYANW
VK         1-35       DIQMTQSPASLSASVGETVTITCRASGNIKNYLAW
T4         1-32       VTQGKTLVLGKEGESAELPCESSQKKITVETW
N-CAM      281-311    LQEGPVAVYTWEGNQVNITCQVFAYPSAVISW
POLY IgT   7-43       LGPSSIFGPGEVNVLEGDSVSITCYYPTTSVNRHSRKFW

FIG. 4C

PROTEIN    RESIDUE    SEQUENCE
FcR        54-77      QASYTFKATVNDSGEYRCQMEQ
FcR        138-160    SNFSIPKANHSHSGDYYCKGSL
VK         92-114     FTLKISRVEAEDLGIYFCSQTT
T4         73-97      FPLTINKLKHEDSQTYICELEN
N-CAM      335-339    SYLEVTPDSENDFGNYNCTAVN
POLY IgT   80-101     FVVTVDQLTQNDSCSYKCGVGV

FIG. 4D

PROTEIN      RESIDUE    SEQUENCE
FcR          80-87      PV----D-LGVIS
FcR          166-173    PV----T-ITVQG
λ J HUMAN    99-111     PVFGGGTKVTVLG
λ J MOUSE    90-110     WVFGGGTKLTVLG

FIG. 8

```
           N  S  G  P  R  N  L  W  L  L  Q  P  L  T  V  L  L  L  L  A   S
          GAATTCCGGTCCCAGAAACCTGTGGCTGCTTCAACCATTGACAGTTTTGCTGCTGCTGGCTT
             10        20        30        40        50        60       70

A  D  S  Q  A  -1 +1
                   A  A  P  P  K  A  V  L  K  L  E  P  P  W  I  N  V  L
          CTGCAGACAGTCAAGCTGCAGCTCCCCCAAAGGCTGTGCTGAAACTTGAGCCCCCGTGGATCAACGTGCT
             80        90       100       110       120       130      140

Q  E  D  S  V  T  L  T (C) Q  G  A  R  S  P  E  S  D  S  I  Q  W  F
          CCAGGAGGACTCTGTGACTCTGACATGCCAGGGGGCTCGCAGCCCTGAGAGCGACTCCATTCAGTGGTTC
            150       160       170       180       190       200      210
                                                                           *
       H  N  G  N  L  I  P  T  H  T  Q  P  S  Y  R  F  K  A  N  N  N  D  S  G
          CACAATGGGAATCTCATTCCCACCCACACGCAGCCCAGCTACAGGTTCAAGGCCAACAACAATGACAGCG
            220       230       240       250       260       270      280

E  Y  T (C) Q  T  G  Q  T  S  L  S  D  P  V  H  L  T  V  L  S ↓G  Q
          GGGAGTACACGTGCCAGACTGGCCAGACCAGCCTCAGCGACCCTGTGCATCTGACTGTGCTTTCCGGTCA
            290       300       310       320       330       340      350

W  R  K  A  P  G  W  T  W  E  G  P  G  R  M  K  S  V  Y  R  Q  R  F
          GTGGAGGAAGGCCCCAGGGTGGACCTGGGAGGGGCCAGGACGGATGAAATCTGTTTACAGACAGAGGTTT
            360       370       380       390       400       410      420

A  G  K  S  G  R  G  L  L  T  G  K  H  C ↓* W  L  V  L  Q  T  P  H  L
          GCAGGAAAGAGTGGGCGTGGACTGCTTACTGGGAAGCACTGTTAATGGCTGGTGCTCCAGACCCCTCACC
            430       440       450       460       470       480      490

E  F  Q  E  G  E  T  I  M  L  R (C) H  S  W  K  D  K  P  L  V  K  V
          TGGAGTTCCAGGAGGGAGAAACCATCATGCTGAGGTGCCACAGCTGGAAGGACAAGCCTCTGGTCAAGGT
            500       510       520       530       540       550      560

T  F  F  Q  N  G  K  S  Q  K  F  S  R  L  D  P  T  F  S  I  P  Q  A
          CACATTCTTCCAGAATGGAAAATCCCAGAAATTCTCCCGTTTGGATCCCACCTTCTCCATCCCACAAGCA
            570       580       590       600       610       620      630
          *
       N  H  S  H  S  G  D  Y  H (C) T  G  N [I  G] Y  T  L  F  S  S  K  P  V
          AACCACAGTCACAGTGGTGATTACCACTGCACAGGAAACATAGGCTACACGCTGTTCTCATCCAAGCCTG
            640       650       660       670       680       690      700

T  I  T  V  Q  V  P  S  M  G  S  S  S  P  M  G  I  I  V  A  V  V  I
          TGACCATCACTGTCCAAGTGCCCAGCATGGGCAGCTCTTCACCAATGGGGATCATTGTGGCTGTGGTCAT
            710       720       730       740       750       760      770

A  T  A  V  A  A  I  V  A  A  V  V  A  L  I  Y  C  R  K  K  R  I  S
          TGCGACTGCTGTAGCAGCCATTGTTGCTGCTGTAGTGGCCTTGATCTACTGCAGGAAAAGCGGATTTCA
            780       790       800       810       820       830      840

A  N  S  T  D  P  V  K  A  A  Q  F  E  P  P  G  R  Q  M  I  A  I  R  K
          GCCAATTCCACTGATCCTGTGAAGGCTGCCCAATTTGAGCCACCTGGACGTCAAATGATTGCCATCAGAA
            850       860       870       880       890       900      910

R  Q  L  E  E  T  N  N  D  Y  E  T  A  D  G  G  Y  M  T  L  N  P  R
          AGAGACAACTTGAAGAAACCAACAATGACTATGAAACAGCTGACGGCGGCTACATGACTCTGAACCCCAG
            920       930       940       950       960       970      980

A  P  T  D  D  K  N  I  Y  L  T  L  P  P  N  D  H  V  N  S  N  N  *
          GGCACCTACTGACGATAAAAACATCTACCTGACTCTTCCTCCCAACGACCATGTCAACAGTAATAACTAA
            990       1000      1010      1020      1030      1040     1050
```

FIG. 9A

|—> Leader	|—>Extracellular
	-1+1

HFc3.1	NSGPRNLWLLQPLTVLLLLASADSQAAAPPKAVLKLEPPWINVLQEDSVTLTCQGARSPESDSIQWF
	*	*		 **	* 	* * **	* ***

Mouse α	MFQNAHSGSQWLLPPLTILLLFAFADRQSAALPKAVVKLDPPWIQVLKEDMVTLMCEGTHNPGNSSTQWF

HFc3.1	HNGNLIPTHTQPSYRFKANNNDSGEYTCQTGQTSLSDPVHLTVLSGQWRKAPGWTWEGPGRHKSVYRQRF
	***	*	 *	**** 	 *  *

Mouse α	HNGRSIRSQVQASYTFKATVNDSGEYRCQMEQTRLSDPVDLGVISD----------------------

HFc3.1	AGKSGRGLLTGKHCXWLVLQTPHLEFQEGETIMLRCHSWKDKPLVKVTFFQNGKSQKFSRLDPTFSIPQA
	 	 **** *	* ****	   ****	*

Mouse α	--------WLLLQTPQRVFLEGETITLRCHSWRNKLLNRISFFHNEKSVRYHHYKSNFSIPKA
	|—>Transmembrane	|—>Cytoplasmic HFc3.1	NHSHSGDYHCTGNIGYTLFSSKPVTITWQVPSMGSSSPMGIIVAVVIATAVAAIVAAVVALIYCRKKRIS
	********	* *	 ****	* **

Mouse α	NHSHSGDYYCKGSLGSTQHQSKPVTITVQDPATTSSISLVWYHTAFSLVMCLLFAVDTGLYFYVRRNLQT

HFc3.1	ANSTDPVKAAQFEPPGRQMIAIRKRQLEETNNDYETADGGYMTLNPRAPTDDKNIYLTLPPNDHVNSNN
	*

Mouse α	PREYWRKSLSIRKHQAPQDK

FIG. 9B

```
         |--->Leader        |--->Extracellular
                           -1 +1

HFc3.1            NSGPRNLWLLQPLTVLLLLASADSQAA-AP--PKAVLKLEPPWINVLQEDSVTLTCQGARSPESDSIQW
                   *          *   **           **     ****  ********  ** ***** *  * **
Mouse B1  MESNWTVHVFSRTLCHMLLWTAVLNLAAGTHDLPKAVVKLEPPWIQVLKEDTVLTCEGTHNPGNSSTQW HFc3.1    FHNGNLIPTHTQPSYRFKANNNDSGEYTCQTGQTSLSDPVHLTVLSGQWRKAPGWTWEGPGRMKSVYRQR
          **       *   *    * ****    ****  *    *
Mouse B1  FHNGRSIRSQWQASYTFKATVNDSGEYRCQMEQTRLSDPVDLGVISD------------------------

HFc3.1    FAGKSGRGLLTGKHCXWLVLQTPHLEFQEGETIMLRCHSWKDKPLVKVTFFQNCKSQKFSRLDPTFSIPQ
                                   ** **  * ****** ** * **   ** *         ****
Mouse B1  -----------WLLLQPTQLVFLEGETITLRCHSWRNKLLNRISFFHNEKSVRYHHYSSNFSIPK
                                |--->Transmembrane           |--->Cytoplasmic HFc3.1    ANMSHSGDYHCTGNIGYTLFSSKPVTITVQVPSMGSSSPMGIIVAVVIATAVAAIVAAVVALIYCRKKRI
          **********  *    *    ******       *  *  **** **    
Mouse B1  ANMSHSGDYYCKGSLGRTLHQSKPVTITVQGPKSSRSLPVLTIVAAVTGIAVAAIVIILVSLVYLKKKQV HFc3.1    SANSTDPVKAAQFEPPGRQMIAIRKRQLEETNNDYETADGGYMTLNPRAPTDDKNIYLTLPPNDHVNSNN
            *     *       *            *           *                     *
Mouse B1  PALPGNPDHREMGETLPEEVGEYRQPSGGSVPVSPGPPSGLEPTSSSPYNPPDLEEAPKTEAENTITYSL Mouse B1  LKHPEALDEETEHDYQNHI
```

```
          N  S  G  P  R  N  L  W  L  L  Q  P  L  T  V  L  L  L  L  A  S  A  D  S
       GAATTCCGGTCCCAGAAACCTGTGGCTGCTTCAACCATTGACAGTTTTGCTGCTGCTGGCTTCTGCAGACAG
              10        20        30        40        50        60        70
               -1 +1
        Q  A  A  P  P  K  A  V  L  K  L  E  P  P  W  I  N  V  L  Q  E  D  S
       TCAAGCTGCAGCTCCCCCAAAGGCTGTGCTGAAACTTGAGCCCCCGTGGATCAACGTGCTCCAGGAGGACTC
              82        92       102       112       122       132       142

V  T  L  T ©  Q  G  A  R  S  P  E  S  D  S  I  Q  H  F  H  N  G  N  L
       TGTGACTCTGACATGCCAGGGGGCTCGCAGCCCTGAGAGCGACTCCATTCAGTGGTTCCACAATGGGAATCT
              154       164       174       184       194       204       214
                                                     *
         I  P  T  H  T  Q  P  S  Y  R  F  K  A  N  N  N  D  S  G  E  Y  T © Q
       CATTCCCACCCACACGCAGCCCAGCTACAGGTTCAAGGCCAACAACAATGACAGCGGGGAGTACACGTGCCA
              226       236       246       256       266       276       286

T  G  Q  T  S  L  S  D  P  V  H  L  T  V  L  S  E  W  L  V  L  Q  T  P
       GACTGGCCAGACCAGCCTCAGCGACCCTGTGCATCTGACTGTGCTTTCCGAATGGCTGGTGCTCCAGACCCC
              298       308       318       328       338       348       358

H  L  E  F  Q  E  G  E  T  I  M  L  R ©  H  S  W  K  D  K  P  L  V  K
       TCACCTGGAGTTCCAGGAGGGAGAAACCATCATGCTGAGGTGCCACAGCTGGAAGGACAAGCCTCTGGTCAA
              370       380       390       400       410       420       430

V  T  F  F  Q  N  G  K  S  Q  K  F  S  R  L  D  P  T  F  S  I  P  Q  A
       GGTCACATTCTTCCAGAATGGAAAATCCCAGAAATTCTCCCGTTTGGATCCCACCTTCTCCATCCCACAAGC
              442       452       462       472       482       492       502
         *
         N  H  S  H  S  G  D  Y  H © T  G  N  I  G  Y  T  L  F  S  S  K  P  V
       AAACCACAGTCACAGTGGTGATTACCACTGCACAGGAAACATAGGCTACACGCTGTTCTCATCCAAGCCTGT
              514       524       534       544       554       564       574

T  I  T  V  Q  V  P  S  M  G  S  S  S  P  M  G  I  I  V  A  V  V  I  A
       GACCATCACTGTCCAAGTGCCCAGCATGGGCAGCTCTTCACCAATGGGGATCATTGTGGCTGTGGTCATTGC
              586       596       606       616       626       636       646

T  A  V  A  A  I  V  A  A  V  V  A  L  I  Y  C  R  K  K  R  I  S  A  N
       GACTGCTGTAGCAGCCATTGTTGCTGCTGTAGTGGCCTTGATCTACTGCAGGAAAAAGCGGATTTCAGCCAA
              658       668       678       688       698       708       718

S  T  D  P  V  K  A  A  Q  F  E  P  P  G  R  Q  M  I  A  I  R  K  R  Q
       TTCCACTGATCCTGTGAAGGCTGCCCAATTTCAGCCACCTGGACGTCAAATGATTGCCATCAGAAAGAGACA
              730       740       750       760       770       780       790

L  E  E  T  N  N  D  Y  E  T  A  D  G  G  Y  M  T  L  N  P  R  A  P  T
       ACTTGAAGAAACCAACAATGACTATGAAACAGCTGACGGCGGCTACATGACTCTGAACCCCAGGGCACCTAC
              802       812       822       832       842       852       862

D  D  K  N  I  Y  L  T  L  P  P  N  D  H  V  N  S  N  N  *
       TGACGATAAAAACATCTACCTGACTCTTCCTCCCAACGACCATGTCAACAGTAATAACTA
              874       884       894       904       914       924
```

FIG. 12A

|→Leader  |→Extracellular
           -1 +1

HFc3.0      NSGPRNLWLLQPLTVLLLLASADSQAAAPPKAVLKLEPPWINVLQEDSVTLTCQGARSPESDSIQWF
            *   * *    **  *** * * ***
Mouse α     MFQNAHSGSQWLLPPLTILLLFAFADRQSAALPKAVKLDPPWIQVLKEDMVTLMCEQTHNPGNSSTQWF HFc3.0      HNGNLIPTHTQPSYRFKANNNDSGEYTCQTGQTSLSDPVHLTVLSEWLVLQTPHLEFQEGETIMLRCHSW
            *** *   * * *    ******   *  *** *  ****   *     ******
Mouse α     HNGRSIRSQWQASYTFKATVNDSGEYRCQMEQTRLSDPVDLGVISDWLLLQTPQRVFLEGETITLRCHSW

|→Transmembrane
HFc3.0      KDKPLVKVTFFQNGKSQKFSRLDPTFSIPQANHSHSGDYHCTGNIGYTLFSSKPVTITVQVPSMGSSSPM
            * *              ** ********  *  *  *     **** *    **
Mouse α     RMKLLNRISFFHNEKSVRYHHYKSNFSIPKANHSHSGDYYCKGSLGSTQHQSKEVTITVQDPATTSSISL

|→ Cytoplasmic
HFc3.0      GIIVAVVIATAVAAIVAAVVALIYCRKKRISANSTDPVKAAQFEPPGRQMIAIRKRQLEETNNDYETADG
            * *                                                **
Mouse α     VWYHTAFSLVMCLLFAVDTGLYFYVRRNLQTPREYWRKSLSIRKHQAPQDK HFc3.0      GYMTLNPRAPTDDKNIYLTLPPNDHVNSNN

FIG. 12B

|———>Leader  |———>Extracellular
                -1 +1

HFc3.0    NSGPRNLHLLQPLTVLLLLLASADSQAA--AP--PKAVLKLEPPWINVLQEDSVTLTCQGARSPESDSIQW
          *           *                 ****   *** *  *   
Mouse β1  MESNWTVHVFSRTLCHLLWTAVLNLAAGTHDLPKAVVKLEPPWIQVLKEDTVTLTCEGTHNPGNSSTQW HFc3.0    FHNGNLIPTHTQPSYRFKANNNDSGEYTCQTGQTSLSDPVHLTVLSEWLVLQTPHLEFQEGETIMLRCHS
          ****  *  *  * **  ******    *  ** *  ****    *  *** *
Mouse β1  FHNGRSIRSQVQASYTFKATVNDSGEYRCQMEQTRLSDPVDLGVISDWLLLQPTQLVFLEGETITLRCHS HFc3.0    WKDKPLVKVTFFQNGKSQKFSRLDPTFSIPQANHSHSGDYHCTGNIGYTLFSSKPVTITVQVPSMGSSSP
           * *     * *  ** *       ******   *  ********* *  * *
Mouse β1  WRNKLLNRISFFHNEKSVRYHHYSSNFSIPKANHSHSGDYYCKGSLGRTLHQSKPVTITVQGPKSSRSLP

|———>Transmembrane
HFc3.0    MGIIVAVVIATAVAAIVAAVVALIYCRKKRISANSTDPVKAAQFEPPGRQMIAIRKRQLEETNNDYETAD
          *** *      ******     * **                *
Mouse β1  VLTIVAAVTGIAVAAIVIILVSLVYLKKKQVPALPGNPDHREMGETLPEEVGEYRQPSGGSVPVSPGPPS HFc3.0    GGYMTLNPRAPTDDKNIYLTLPPNDHVNSNN
           *              *
Mouse β1  GLEPTSSSPYNPPDLEEAPKTEAENTITYSLLKHPEALDEETEHDYQNHI

FIG. 13

28s -

18s -

A  B  C

DNA ENCODING FOR AN FC RECEPTOR FOR IMMUNOGLOBULIN

This application is a continuation of application Ser. No. 07/174,991, filed Mar. 1, 1988, now abandoned.

This invention relates to a FC receptor for immunoglobulin.

In one aspect this invention relates to cDNA clones encoding the murine and human Fc receptor for IgG. The murine clones were sequenced and expression of mRNA and the cell surface Fc receptor investigated. The murine Fc receptor is a 301 amino acid transmembrane glycoprotein with two homologous extracellular domains that are also homologous to members of the Ig superfamily. The Fc receptor has 4 sites of N linked glycosylation and a long 94 amino acid cytoplasmic tail. Northern analysis of mRNA, immune complex binding and serological studies of cell lines and transfectants demonstrated that the receptor encoded by the cDNA clone binds murine IgG2b and possibly other Ig. Human Fc(gamma)R cDNA clones were also isolated and found to encode a glycosylated transmembrane molecule that bears striking homology to both the beta1 and alpha mouse FcR at both the nucleic and amino acid levels.

The present invention provides a receptor for the Fc portion of immunoglobulin and being derived from ATCC 67414, ATCC 67415 or ATCC 67416.

The present invention provides a receptor for the Fc portion of immunoglobulin, the receptor exhibiting the ability to bind to the Fc portion of mouse and human immunoglobulin.

The receptor preferably exhibits an ability to bind to antibodies and immune complexes, has
a size of 40–70 kilodaltons,
is formed from mRNA of a size of about 1.8, about 2.0, about 1.9, about 1.4 or about 2.4 kilobases, and
includes two substantially regularly spaced pairs of Cys residues, two or four potential N-linked glycosylation sites. The present invention includes a receptor for the Fc portion of immunoglobulin and having at least 40%, more preferably at least 50% and still more preferably at least 60% homology with the above receptor.

In one instance the receptor includes the amino acid sequences:
(a) met leu leu trp thr ala val leu asn leu ala ala gly thr his asp leu pro lys ala val val lys leu glu pro pro trp ile,
(b) glu gln thr arg leu ser asp pro val asp leu gly val ile, and
(c) lys gly ser leu gly arg thr leu his gln ser lys pro val thr ile thr val gln gly pro lys, and
(d) glu ala glu asn thr ile thr tyr ser leu leu lys his pro glu ala leu asp glu glu thr glu his.

In a preferred instance the receptor includes at least one of the amino acid sequences:
(a) Met Glu Ser Asn Trp Thr Val His Val Phe Ser Arg Thr Leu Cys His Met Leu Leu Trp Thr Ala Val Leu Asn Leu Ala Ala Gly.
(b) Cys Glu Gly Thr His Asn Pro Gly Asn Ser Ser Thr Gln Trp Phe His Asn Gly Arg Ser ILE Arg Ser Gln Val Gln Ala Ser Tyr Thr Phe Lys Ala Thr Val Asn Asp Ser Gly Glu Tyr Arg Cys.
(c) Cys His Ser Trp Arg Asn Lys Leu Leu Asn Arg Ile Ser Phe Phe His Asn Glu Lys Ser Val Arg Tyr His His Tyr Ser Ser Asn Phe Ser Ile Pro Lys Ala Asn His Ser His Ser Gly Asp Tyr Tyr Cys.
(d) Leu Pro Val Leu Thr Ile Val Ala Ala Val Thr Gly Ile Ala Val Ala Ala Ile Val Ile Ile Leu Val Ser Leu Val Tyr Leu.
(e) Lys Lys Lys Gln Val Pro Ala Leu Pro Gly Asn Pro Asp His Arg Glu Met Gly Glu Thr Leu Pro Glu Glu Val Gly Glu Thr Arg Gln Pro Ser Gly Gly Ser Val Pro Val Ser Pro Gly Pro Pro Ser Gly Leu Glu Pro Thr Ser Ser Ser Pro Tyr Asn Pro Pro Asp Leu Glu Glu Ala Pro Lys Thr Glu Ala Glu Asn Thr Ile Thr Tyr Ser Leu Leu Lys His Pro Glu Ala Leu Asp Glu Glu Thr Glu His Asp Tyr Gln Asn His Ile.
(f) N S G P R N L W L L Q P L T V L L L L A S A D S Q A A.
(g) C Q G A R S P E S D S I Q W F H N G N L I P T H T Q P S Y R F K A N N N D S G E Y T C.
(h) C H S W K D K P L V K V T F F Q N G K S Q K F S R L D P T F S I P Q A N H S H S G D Y H C.
(i) S P M G I I V A V V I A T A V A A I V A A V V A L I Y C.
(j) R K K R I S A N S T D P V K A A Q F E P P G R Q M I A I R K R Q L E E T N N D Y E T A D G G Y M T L N P R A P T D D K N I Y L T L P P N D H V N S N N.

The present invention also provides a nucleotide sequence, gene cDNA clone, or a vector for same adapted to encode or to produce a material adapted to encode for the receptor above or a fragment thereof.

The present invention also provides a nucleotide sequence, gene, cDNA clone, or a vector for same adapted to encode or produce a material adapted to encode for the leader sequence, extracellular region, transmembrane region or intracellular region of the receptor above.

The present invention also provides a cDNA clone, gene or nucleotide sequence being incorporated in ATCC, ATCC or ATCC and capable of encoding for a receptor for the Fc portion of immunoglobulin or a fragment thereof and a material being ATCC, ATCC, or ATCC.

A preferred nucleotide sequence, cDNA clone, gene or vector containing same and capable of encoding for a receptor for the Fc portion of immunoglobulin includes the nucleotide sequences:
(a) ATG CTA CTG TGG ACA GCC GTG CTA AAT CIT GCT GCT GGG ACT CAT GAT CTT CCA AAG GCT GTG GTC AAA CTC GAG CCC CCG TGG ATC,
(b) GAG CAG ACC CGC CTC AGC GAC CCT GTA GAT CTG GGA GIG ATT,
(c) AAA GGA AGT CTA GGA AGG ACA CTG CAC CAG TCC AAG CCT GTC ACC ATC ACT GTC CAA GGG CCC AAG, and
(d) GAG GCT GAG AAC ACG ATC ACC TAC TCA CTC CTC AAG CAT CCC GAA GCC TTG GAT GAA GAA ACA GAG CAT.

In a preferred instance the nucleotide sequence, cDNA done, gene or vector containing same includes at least one of the nucleotide sequences:
(a) ATG GAG AGC AAC TGG ACT GTC CAT GTG TTC TCA CGG ACT TTG TGC ATG CTA CTG TGG ACA GCC GTG CTA AAT CTT GCT GCT GGG.

(b) TGC GAA GGG ACC CAC AAC CCT GGG
AAC TCT TCT ACC CAG TGG TTC CAC
AAT GGG AGG TCC ATC CGG AGC CAG
GTC CAA GCC AGC TAC ACG TIT AAG
GCC ACA GTC AAT GAC AGT GGA GAA
TAT CGG TGT.

(c) TGC CAT AGC TGG AGG AAC AAA CTA
CTG AAC AGG ATC TCG TTC TTC CAT
AAT GAA AAA TCC GTG AGG TAT CAT
CAC TAC AGT AGT AAT TTC TCT ATC
CCC AAA GCC AAC CAC AGT CAC AGT
GGG GAC TAC TAC TGC.

(d) TTA CCA GTA TTG ACA ATT GTG GCT
GCT GTC ACT GGG ATT GCT GTC GCA
GCC ATT GTT ATT ATC CTA GTA TCC
TTG GTC TAT CTC.

(e) AAG AAA AAG CAG GTT CCA GCT CTC
CCA GGA AAC CCT GAT CAC AGG GAA
ATG GGA GAA ACC CTT CCA GAG GAA
GTA GGT GAG TAC AGA CAG CCC TCT
GGG GGC TCA GTG CCT GTC AGC CCA
GGG CCT CCA TCT GGA CTG GAG CCA
ACA AGC AGC AGC CCA TAC AAT CCT
CCT GAT CTG GAA GAA GCT CCC AAA
ACT GAG GCT GAG AAC ACG ATC ACC
TAC TCA CTC CTC AAG CAT CCC GAA
GCC TTG GAT GAA GAA ACA GAG CAT
GAT TAC CAA AAC CAC ATT TAG.

(f) AAT TCC GGT CCC AGA AAC CTG TGG
CTG CTT CAA CCA TTG ACA GTT TTG
CTG CTG CTG GCT TCT GCA GAC AGT
CAA GCT GCA.

(g) TGC CAG GGG GCT CGC AGC CCT GAG
AGC GAC TCC ATT CAG TGG TTC CAC
AAT GGG AAT CTC ATT CCC ACC CAC
ACG CAG CCC AGC TAC AGG TTC AAG
GCC AAC AAC AAT GAC AGC GGG GAG
TAC ACG TGC.

(h) TGC CAC AGC TGG AAG GAC AAG CCT
CTG GTC AAG GTC ACA TTC TTC CAG
AAT GGA AAA TCC CAG AAA TIC TCC
CGT TTG GAT CCC ACC TTC TCC ATC
CCA CAA GCA AAC CAC AGT CAC AGT
GGT GAT TAC CAC TGC.

(i) TCA CCA ATG GGA ATC AFT GTG GCT
GTG GTC ATT GCT ACT GCT GTA GCA
GCC ATT GTT GCT GCT GTA GTG GCC
TTG ATC TAC TGC.

(j) AGG AAA AAG CGG ATT TCA GCC AAT
TCC ACT GAT CCT GTG AAG GCT GCC
CAA TTT GAG CCA CCT GGA CGT CAA
ATG ATT GCC ATC AGA AAG AGA CAA
CTT GAA GAA ACC AAC AAT GAC TAT
GAA ACA GCT GAC GGC GGC TAC ATG
ACT CTG AAC CCC AGG GCA CCT ACT
GAC GAT AAA AAC ATC TAC CTG ACT
CTT CCT CCC AAC GAC CAT GTC AAC addition or substitution of amino acids or by chemical or irradiation modification not substantially deleteriously affecting the ability to bind to the Fc portion of immunoglobulin and a nucleotide sequence, gene, cDNA clone, or a vector for same as above and modified by deletion, addition or substitution of nucleotides or by chemical or irradiation modification not substantially deleteriously affecting the ability to code for a receptor for the Fc portion of immunoglobulin or a fragment thereof.

DESCRIPTION OF PREFERRED ASPECTS

Fc receptors (FcR) form a major groups of cell membrane glycoproteins involved in homeostasis of the immunological system. Specific receptors for all immunoglobulin (Ig) classes have been defined and are found on a wide variety of immune cells—B cells and some T cells as well as myeloid cells and non-haemopoietic cells (Hubscher et at, 1971; Dickler, 1976; Tsay et at, 1980; Unkless et at, 1981 ). The principal role of these receptors is to bind (Ig) via the Fc region of the Ig molecule and it is through this interaction that a wide range of biological effects are mediated. These include phagocytosis of immune complexes by macrophages (Leslie, 1980) and neutrophils (Capron et at, 1984) and direct or indirect regulation of antibody production by membrane bound or soluble Fc receptor (Yodoi et at, 1980; Fridman et at, 1981; Kolsch et at, 1983). In the murine system efforts have been devoted to the analysis of the receptor for IgG1/IgG2b (Fc(gamma)1/(gamma)2bR) which is important in the binding of immune complexes (Unkless, 1974; Kurlander et at, 1984). To investigate these receptors further at both the structural and functional level, as well as to study its relationship to other FcR, we have produced a monoclonal anti-Ly-17.2 antibody that defines a genetic polymorphism of the Fc(gamma)R genes (Hibbs et at, 1985). This antibody was used to immunopurify receptors for which we have:

1. isolated and determined the partial amino acid;
2. isolated and determined the complete nucleotide sequence of cDNA clones termed pFC24 and pFC113 encoding the beta1 Fc(gamma)R receptor.
3. Shown by Northern analysis the presence of multiple FcR transcripts in different cell types, these variant transcripts are termed beta2 and alpha.
4. Using the mouse FcR cDNA and oligonucleotide probes (based on pFC 113 DNA sequence) isolated cDNA clones termed pFC 3.0, 3.1 and 3.47 encoding human FcRs that are homologous to the mouse FcR.

Monoclonal Antibodies: The monoclonal anti-Ly-17.2 and Ly-2.1 antibodies have been previously described (Hibbs et al 1985, Hogarth et al 1982). Preparation of F(ab')$_2$ fragments from purified antibody was performed as described (16). The 2.4 G2 antibody has also been described before (Unkless 1979).

Purification of FcgammaR: J774 macrophage cells ($2 \times 10^{10}$) were harvested from ascites fluid obtained from (CBA×BALB/c)F1 mice and immediately lysed in cold phosphate buffered saline (PBS)/0.5% Nonidet P-40 (PBS/0.5% NP40) pH 7.4 containing 1% aprotinin (Sigma, St. Louis, Mo.) and 1 mM phenylmethylsulfonyl fluoride (Sigma, St. Louis, Mo.). An additional $2 \times 10^7$ cells were surface labelled with $^{125}$I, and pooled with the cold lysate. After lysis for 1 hour at 4° C., the lysates were clarified and incubated for 1 hour at 4° C. with anti-Ly-17.2 antibody conjugated Sepharose 48 (Pharmacia, Uppsala, Sweden). The immunoabsorbent was washed three times in 0.6M NaCl, 0.0125M KH$_2$PO$_4$, pH 7.4, three times in PBS/0.5% NP40 pH 7.4 and a further three times in 0.5% deoxycholate in 100 mM Tris-HCl pH 8.0. The immunoabsorbent was packed into a column and the bound material eluted with 0.5% sodium dodecyl sulfate (NaDodSO$_4$) in 0.1M triethylamine pH 11.5 and freeze dried.

The purity of the Fc gamma R preparations was assessed by NaDodSO$_4$/polyacrylamide gel electrophoresis (NaDodSO₄/PAGE) and proteins were detected by Coomassie blue staining or by autoradiography.

Protein Sequence Analysis: Protein samples were carboxamidomethylated and ethanol precipitated prior to sequencing. Briefly, samples were dissolved in 50 mM boric acid, 0.1% (w/v) SDS and 10 mM dithiothreitol pH 8.0 (NaOH) and heated to 60° C. for 1 hour. Iodoacetamide was added to a final concentration of 22 mM and the samples incubated for 15 minutes at ambient temperature in the dark. Ice cold ethanol containing 50 mM HCl was added and the protein allowed to precipitate at −20° C. for 2 hours. The precipitate was collected by centrifugation, dissolved in $CF_3COOH$ and sequenced by automatic Edman degradation using an Applied Biosystems 470A Sequencer (Foster City, Calif., USA) Sequencing and phenylthiohydantoin amino acid identification techniques have previously been described in detail.

Preparation of FcgammaR Peptides: FcgammaR peptides were obtained by digesting samples of affinity purified, carboxamidomethylated Fc gamma R with either S. aureus V8 protease (Miles Laboratories) (Hibbs et al 1986) lysine-C-proteinase (according to manufacturers instructions, Boehringer Mannheim, Mannheim, FRG) or cyanogen bromide (CNBr). Peptides were purified by reverse phase chromatography using a Pharmacia fast protein liquid chromatography (FPLC). The proteinase digested material was applied to a Pep RPC HR5/5 (C2/C18) reverse phase column (Pharmacia) while a Pro RPC HR 5/10 (C1/C8) reverse phase column (Pharmacia) was used to purify CNBr peptides. Peptides were eluted with ascending linear acetonitrile gradients using 20 mM ammonium formate as a buffer and an absorbance trace at 214 nm to detect peptide peaks. Selected peak fractions were then rechromatographed on the same column again using linear gradients of acetonitrile but in this case containing 0.1% (v/v) unbuffered $CF_3COOH$ to promote ion suppression.

Preparation of Oligonucleotide Probes: Oligodeoxynucleotide probes were synthesized by the phosphoramidite method using an Applied Biosystems 380A DNA Synthesizer. The oligonucleotide probes were purified from crude mixtures by reverse phase HPLC and were radiolabeled with [gamma³²P]ATP and T4 polynucleotide kinase to $2 \times 10^8$ dpm/ug (Maniatis et al 1982).

Library Screening: The cDNA library used in the murine study was kindly provided by Drs N. Gough and A. Dunn (Ludwig Institute for Cancer Research, Melbourne, Australia) and was constructed using poly A+ mRNA from the FcR+ myelomonocytic cell line WEHI 38 (Gough et al, 1985). The cDNA was GC tailed into the SacI site of the pJL3 vector, with the result that all cDNA inserts are flanked by EcoRI sites. Oligodeoxynucleotide probes (Tables 2,3) were constructed using the phosphoramidite method (Winnaker and Dorpoer, 1982) and were complementary to mRNA for use in Northern Analysis. The cDNA library was screened with end labelled oligonucleotide probes using T4 polynucleotide kinase to $>10^9$ dpm/ug DNA. Hybridisation and washing conditions were as previously described (Hibbs et al., 1986).

Northern Blot Analysis of RNA: Poly A + mRNA was obtained from lysates of in vitro grown mouse cells and normal human spleen. PolyA+ mRNA (5 ug of polyA +or variable amounts of total mRNA) was denatured and electrophoresed in 1% agarose gels formaldehyde, transferred to nylon membrane and hybridised overnight (Maniatis et at, 1982). Hybridisations with the cDNA probe were performed in 5×SSPE, 0.1% SDS, 50% formamide, 0.125% skim milk powder and 1 ug/ml degraded DNA, at 42° C. for 16 hrs. The filters were then washed twice in 1×SSPE at room temperature, then twice in 0.2×SSPE at 50° C. for 16 hrs. Hybridisations with the oligodeoxynucleotide probe were performed in 5×SSPE, 6% SDS, 10×Denhardts and 1 ug/ml degraded salmon sperm DNA at 42° C. Filters were washed twice in 2×SSPE at room temperature then twice in 1×SSPE at 42° C. The cDNA probe was labelled by nick translation and unincorporated label removed on a spinning sepharose G50 column (Maniatis et at, 1982). The oligodeoxynucleotide probe was end labelled with $^{32}P$- ATP for 1 hour at 37° C. using T4 polynucleotide kinase then added directly to the hybridisation mix (Maniatis et at, 1982).

Southern Analysis: DNA was prepared from C57BL/6 mouse spleen, human thymus and peripheral blood (Maniatis et at, 1982); 20 ug of DNA digested with appropriate restriction enzyme according to the manufacturer's instructions (Pharmacia, Uppsala, Sweden) was electrophoresed in a 0.5% agarose gel, transferred to a nylon membrane and hybridised in 5×SSC, 0.1% SDS, 50% formamide, 20 mM phosphate buffer pH 6.8 and 0.125% skim milk powder overnight with randomly primed or nick translated cDNA at 55° C. Filters were washed 4 times in 1×SSC, 0.1% SDS, 0.125% skim milk powder then twice in 0.2×SSC, 0.1% SDS at 55° C., dried and autoradiographed. Southern analysis was performed on cDNA clones pFC24, pFC113, HFc3.47, HFc3.1 and HFc3.0 following EcoRI digestion, electrophoresis on 1% agarose gels followed by transfer to nylon membranes (Hibbs et at, 1986). Filters containing pFc24 or pFc113 were probed as described (Hibbs et at, 1986). Filters containing HFc3.1 HFc3.0 or HFc3.47 were probed with nick translated cDNA or end labelled oligonucleotides by hybridisation at 35° in 20% formamide, 5×SSC, 0.1% SDS, 0.125% skim milk powder for 16 hours then washed in 1×SSC at 35° C.

Detection of FcR by EA rosetting: Sheep erythrocytes were washed four times in normal saline. Packed cells (50 ul) were added to 4 ml of trinitrobenzene sulphonate (12.5 mg/ml in phosphate buffered saline (PBS)) and the pH adjusted to pH 7.2. The mixture was incubated at room temperature for 20′ then washed three times. The cells were resuspended in 20 ml of anti-TNP antibody (K1, IgG2b or A3 IgG1; Lopez et at., 1983) or rabbit IgG anti sheep erythrocytes at a subhaemagglutinating dilution to give IgG2b-EA, IgG 1-EA or rabbit IgG-EA After a 20′ incubation at room temperature, the cells were washed twice and resuspended to 1% in PBS+5% BSA and 10 mM azide. EA rosetting for detection of FcR was then performed using the sensitized erythrocytes (Parish and Haywood, 1974).

Cells lines: The cell lines used in this study were the BALB/c macrophage tumour J774, BALB/c myelomonocytic cell line WEHI 3B, and the AKR thymoma K36. Cell line were maintained in vitro in Dulbecco's modified Eagle's medium or RPMI 1640 both supplemented with 10% fetal calf serum. Serological Detection of Ly-17 (FcR) expression: Cell lines were tested for FcR expression using a monoclonal anti-Ly-17.2 antibody and rosetting with sheep anti-mouse Ig coated erythrocytes (Hibbs et al., 1985; Parish and McKenzie, 1978).

DNA sequencing: The cDNA inserts of pFc24, pFc113 were sequenced by either chemical cleavage described by Maxam and Gilbert (1980) or Sanger dideoxy sequencing (Sanger et at., 1977) after subcloning into M13mp8, M13mp9, or M13mp18 according to the sequencing strategy outlined in FIG. 3A. The cDNA inserts of the human FcR clones were also sequenced by the dideoxy nucleotide method after subcloning fragments into M13 vectors.

Isolation of Human FcR cDNA: A human monocyte library (from the human THP-1 cell line) constructed in the lamdagt10 vector was used to isolate human Fc(gamma)R cDNA. Dual screenings were performed using both the mouse beta1 cDNA clone and a pool of oligonucleotide probes constructed from the nucleotide sequence of the mouse beta1 Fc(gamma)R cDNA. This pool consisted of three unique probes which corresponded to nucleotides 137-185 in the mouse (N-terminus), nucleotides 545-574 (second extracellular domain) and nucleotide 956-1000 (C-terminus). After four rounds of screening, several clones (HFc3.1, 3.0, 3.47) which hybridised with both the murine cDNA and oligonucleotide probe pool were isolated and further characterised. Phage DNA was prepared from these. Southern hybridisation analysis of EcoRI digested lambda DNA confirmed that the murine beta1 Fc(gamma)R cDNA probe hybridised with cDNA inserts from all clones. Probing southern blots of EcoRI digested HFc3.1, 3.0, 3.47 independently with each of the three murine oligonucleotide probes, showed that only the mouse N-terminal probe hybridised to the inserts from HFc 3.1, 3.0 and only the mouse C-terminal probe hybridised to the 1.9kb insert from Hfc3.47. In addition, DNA inserts from HFc3.1, HFc3.0 and HFc3.47 cross-hybridised. The DNA inserts were purified and subcloned into the vector pJL4 to give the recombinant plasmids.

RESULTS AND DISCUSSIONS

Reference is made to the Figures of drawings as follows:

FIGURE LEGENDS

FIGS. 1,A-C. One dimensional NaDodSO4/PAGE analysis of the IgG FcR of J774 macrophage cells. Sizes are given in kDa. (A) Immunoprecipitation of Fc gamma R from surface iodinated J774 cells. Immunoprecipitations were performed with anti-Ly-2.1 F(ab')2 (Lane 1) or with anti-Ly-17.2 F(ab')2 (Lane 2). (B) NaDodSO4/PAGE and Coomassie staining of a typical preparation of affinity purified FcR used for protein sequencing and peptide generation. Lanes 1-6 represent successive fractions of eluted material from the affinity column (C). Autoradiogram of NaDodSO4/PAGE of affinity purified 125I-labeled FcR. Lanes 1-6 are as for B, above.

FIG. 2. Southern blot analysis of pFc24 and pJL3. One microgram of pFc24 (lanes B,D,F) or pJL3 (lanes A,C,E) was digested with EcoRI and electrophoresed in 1% agarose gel. The DNA was transferred onto nitrocellulose and hybridised with [32P] labelled probe 1 (lanes A,B), [32P] probe 2 (lanes G,D) and [32P] probe 3 (lanes E,F). Hinfl fragments of pBR322 DNA were used as markers to estimate the size of the cDNA insert of pFc24 (shown in kb). The relative position of pJL3 is also indicated (5.49kb).

Figure 3A:
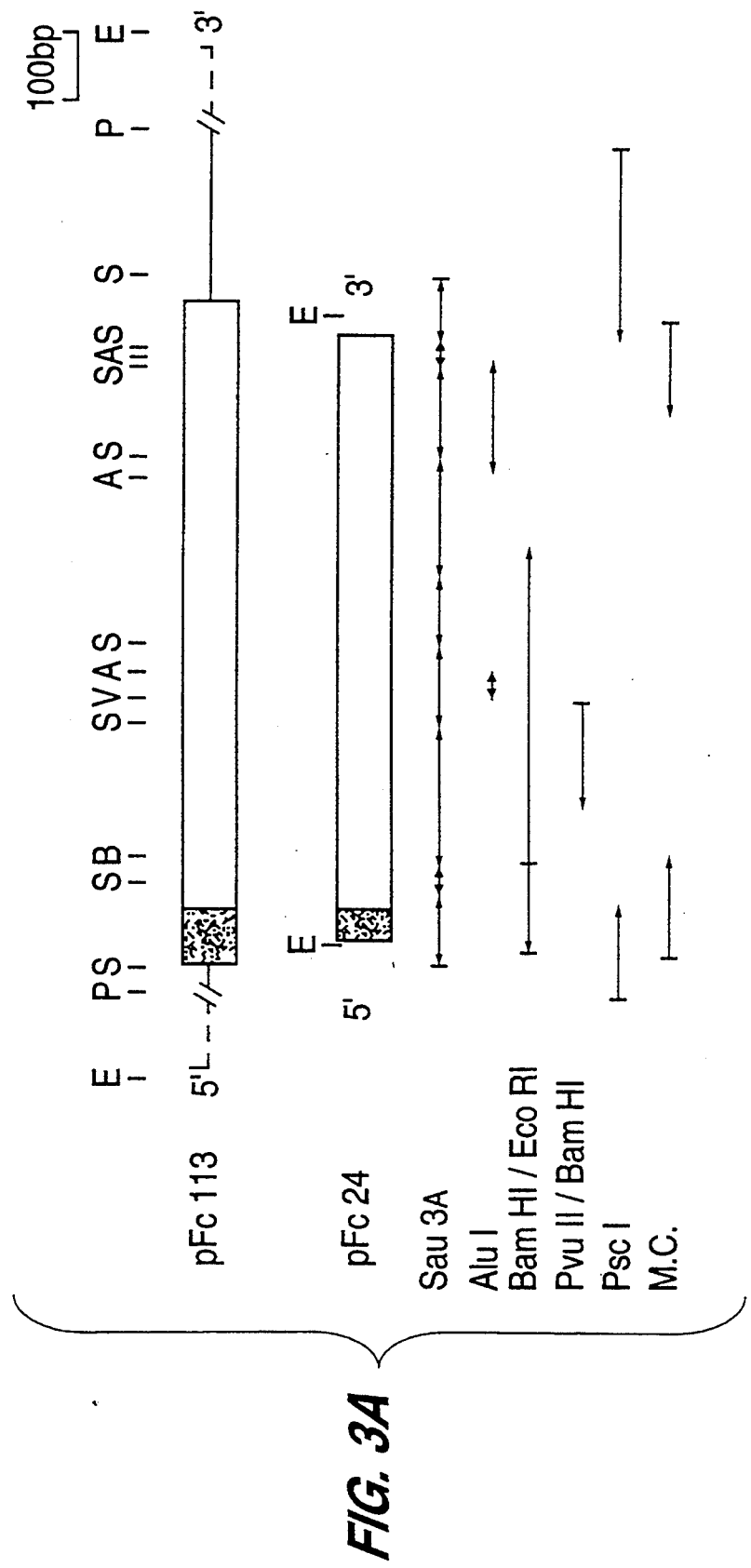

FIGS. 3A-B. (A) Partial restriction map and sequencing strategy for cDNA inserts of clones pFc24 and pFc113. Restriction enzymes sites shown are A, AluI; B, BamHI; E, EcoRI; S, Sau3A1; and V, PvuII. The EcoRI sites shown are present in the polycloning site of the pJL3 vector. The shaded area represents sequence encoding the signal sequence and coding sequence for the mature protein is located within the open box. Sequence from 5' and 3' untranslated regions is indicated by the solid line while unsequenced untranslated regions are represented by the dashed line. Sequence was obtained across all restriction sites except for the PstI sites and both strands of the coding region were entirely sequenced. (B) Nucleotide and deduced amino acid sequence of the mouse FcR encoded by pFc113. Amino acids are numbered above the line in decades commencing at the amino terminal Thr deduced by protein sequencing (Hibbs et al, 1986). Nucleotides are numbered at the end of the line and the 5' and 3' untranslated regions are shown in closed up type. The signal sequence is numbered from residue $-29$ to $-1$ and the transmembrane region (Tm) is underlined by a broken line. The sequences underlined with a solid line correspond to sequences identical to the amino terminal sequence (NH2) and to amino acid sequence of peptides (L9, V17, 2V16, 2V8, CNBR, L5, L3, L4, V10, V11) isolated from the immunopurified FcR (Hibbs et al., 1986). Other notation is as follows: o, first Cys in each domain; O second Cys in each domain; N-linked glycosylation sites. The nucleotide sequence of pFc24 is embodied within the cDNA insert of pFc113 from nucleotides 61 to 1023.

FIGS. 4A-D. Amino acid sequence comparison of Fc(gamma)R domains (amino acids 5-116 for domain 1 and amino acids 118-175 for domain 2) to each other and to Ig related molecules. Identical residues are boxed and a "-" indicates a break in sequence for alignment purposes. (A) The FcR domains were aligned with each other to give the optimal score using the ALIGN program with a matrix bias of $+6$ and break penalty of 6 (see text). (B) Alignment of amino acid sequences around the first Cys residue of both FcR domains with Cys residues of the corresponding first Cys of domains of Ig and Ig related molecules. Amino acids common to FcR domains and other sequences are boxed; $V^2$, MOPC 104E (Apella, 1977); Vk, MOPC 149 (Nishioka and Leder, 1980); T4, L3T4 (Classon et al, 1986; Tourvieille et al, 1986; G. Clark, N. Deacon Personal Communication); N-CAM, Nueral Cell Adhesion Molecule (Hemperly et al, 1986); Poly IgR, Poly Ig Receptor (Mostov et al, 1984). (C) Alignment of sequences around the second Cys of FcR domains with the second Cys of domains of Ig and Ig related molecules as in C above except Vk which is derived from an antidigoxin antibody (Novotny and Margolies, 1983). Common residues are boxed as above. (D) Alignment of lambdaJ regions from human (Engelhard and HHschmann, 1975) and mouse (Apella, 1977), with J-like sequences from the FcR domains.

Figure 5A:
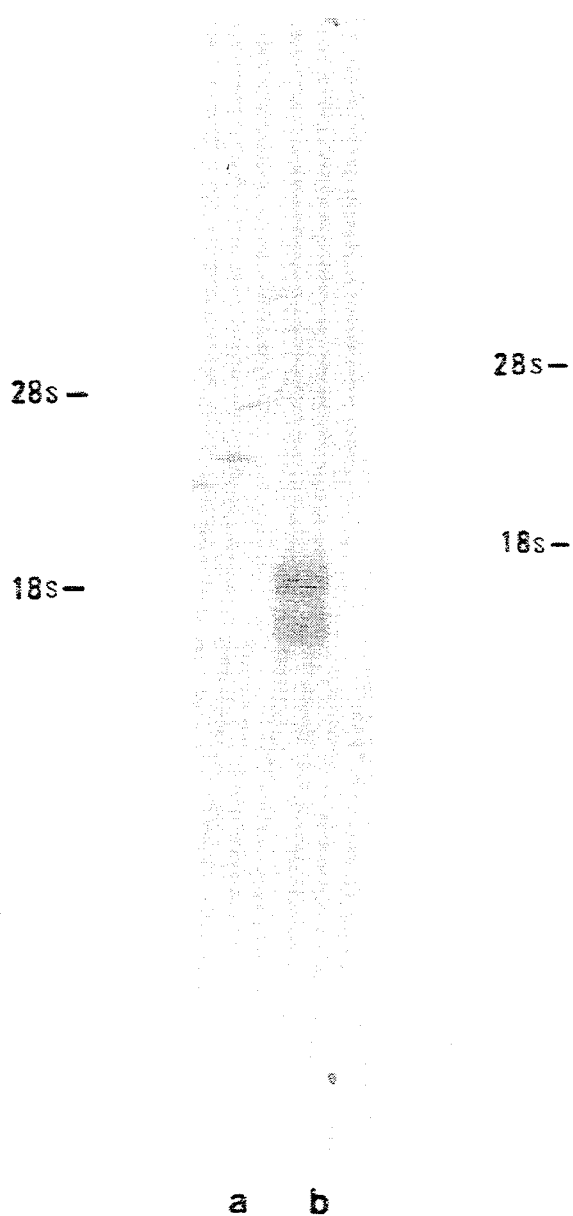
Figure 5B:
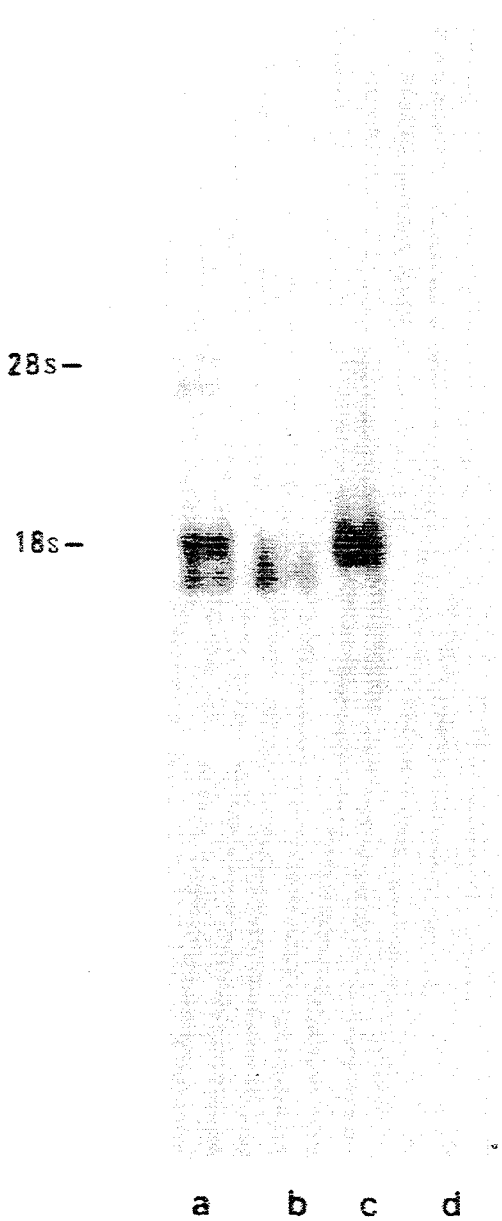

FIGS. 5A-B. Analysis of FcR mRNA transcripts in mouse cell lines. (A) Northern blot of RNA from FcR-erythroleukaemia cells F4N (a) or FcR+WEHI 3B cells (b) probed with 840 base pair 3 am HI-Eco RI fragment of pFc24 (Eco RI site of the vector polycloning site ). (B) Northern blot of poly A+RNA from FcR+cell lines, WEHI 3B (a); J774 macrophage cells (b); K36 T lymphoma (c); and FcR cells F4N (d), probed with an oligodeoxynucleotide corresponding to nucleotides 542-674 in pFc113. The position of 28S and 18S rRNA is indicated.

Figure 6:
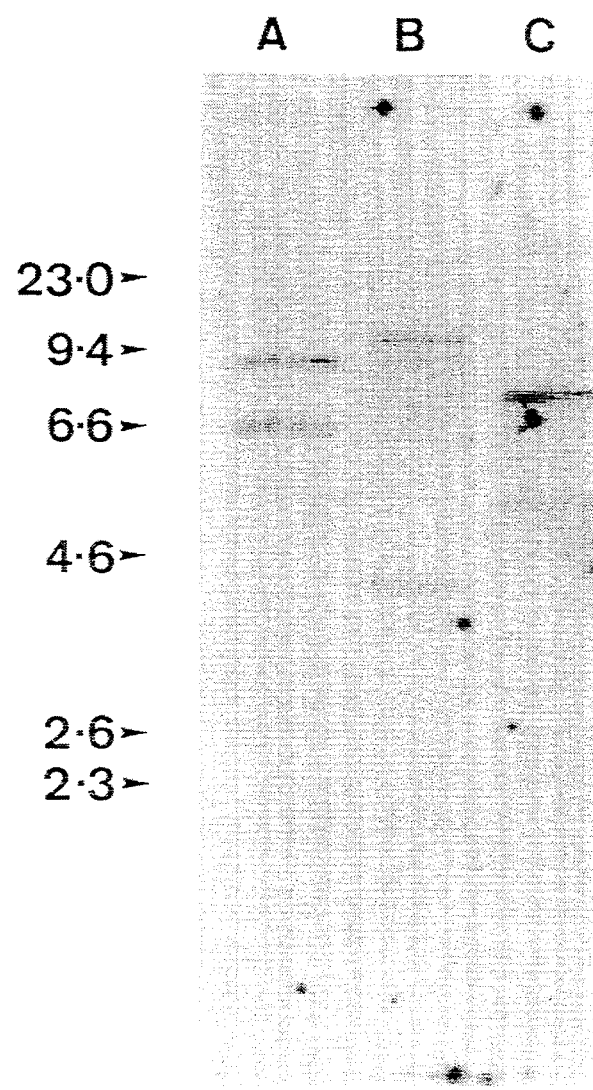

FIG. 6 Southern analysis of the FcR gene. Spleen DNA from C57BL/6 mice was digested with (a) HindIII, (b) EcoRI or (c) PstI and probed with the 840bp BamHI-EcoRI fragment of pFc24 (see Legend FIG. 3). Molecular size-markers in Kb(Hind III digested lamda-phage DNA) are indicated.

Figure 7A:
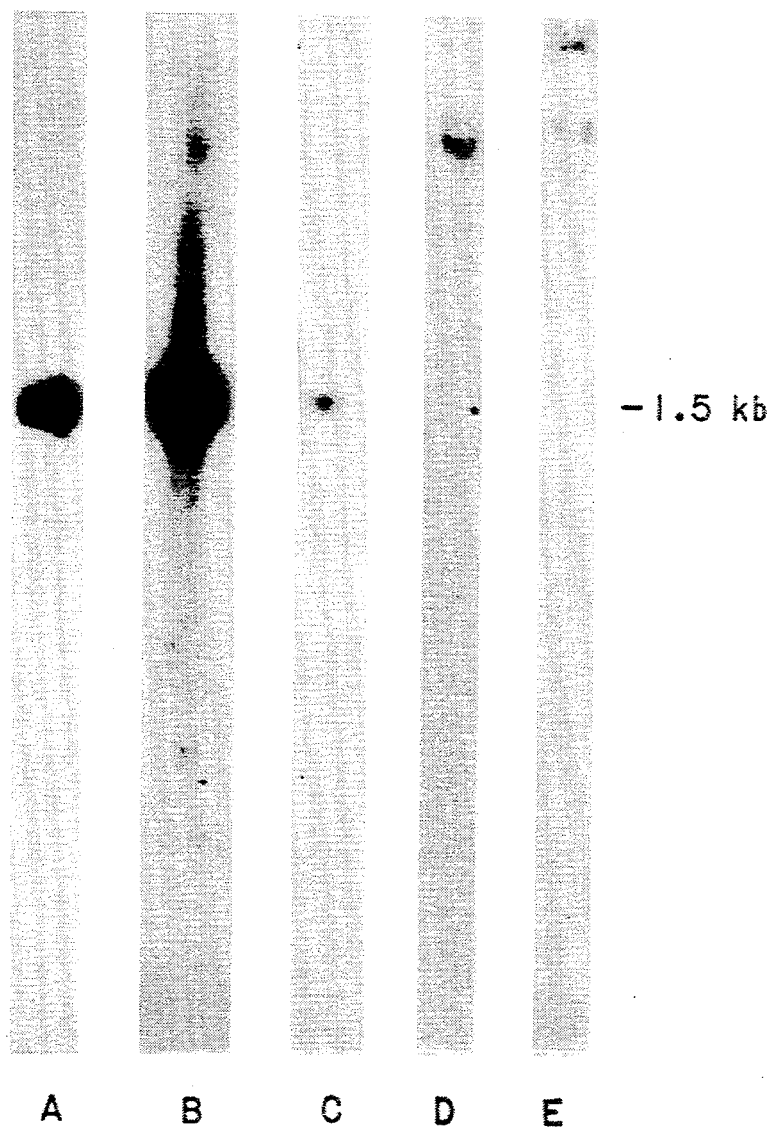
Figure 7B:
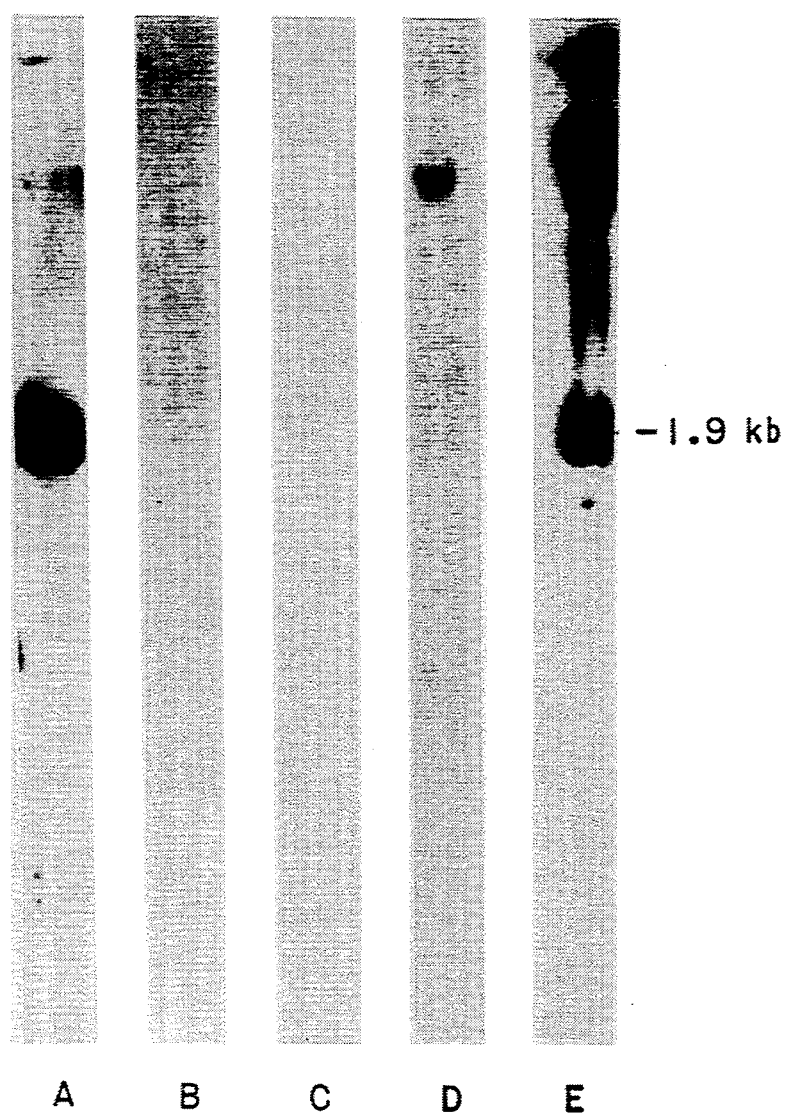

FIGS. 7A-B. Southern blot analysis of human FcR clones HFc3.1 (a) and HFc3.47 (b). HFc3.1 or HFc3.47 DNA was digested with EcoRI and electrophoresed in 1% agarose gel, transferred to nylon membranes as per the materials and methods and hybridised with A, pFc24 cDNA; B, probe 1.5; C, probe 1.10; D, probe alpha or E, probe 1.6. The position of the 1.5 kb cDNA insert of HFc3.1 and of the 1.9 kb insert of HFc3.47 is indicated on the right hand side of each figure.

FIG. 8 Nucleotide and predicted amino acid sequence of the human FcR encoded by HFc3.1 Nucleotides are numbered every decade and the translated sequence is found above the nucleotide sequence. Amino acids are numbered above the line and number 1 indicates the N-terminal residue. The incomplete signal sequence is underlined by a broken line to residue −1. The two glycosylation sites are marked by stars and the single hydrophobic transmembrane region is underlined by a solid line. Cysteine residues involved in disulphide bonding are circled. The "intron-like" sequence is located between the vertical arrows.

FIGS. 9A-B. Homology of the human FcR encoded by HFc3.1 cDNA with the mouse alpha and beta1 Fc(gamma) R. Alignment of the nucleotides of the human FcR with both mouse alpha (A) and beta1 (B) Fc (gamma)R. Breaks (indicated by dashes) in the sequence have been introduced to optimize the alignment. Amino acid residues common to the human FcR encoded by HFc3.1 and the alpha FcR (A) or beta1 (B) are shown by asterisks. The human (HFc3.1), mouse alpha or beta FcR leader sequence, extracellular domain, transmembrane domain and cytoplasmic domains are indicated by the sequences between the vertical arrows. The cysteine (C) residues within the extracellular domains (involved in S—S bonds) are identified by the solid circles.

FIG. 10 Partial nucleotide sequence and predicted amino acid sequence for HFc3.47 cDNA derived from two non-overlapping HFc3.47 fragments and identification of homologous regions in the beta (1 or 2) FcR of the mouse. The HFc3.47 nucleotide and amino acid sequences are shown as the upper sequences in A and the lower sequences in B. Diamonds indicate nucleotide identities where as asterisks indicate amino acid identities. An "X" in the sequence indicates an unknown residue.

FIG. 11 Nucleotide and predicted amino acid sequence of the human FcR encoded by HFc3.0. Nucleotides are numbered every decade and the translated sequence is found above the nucleotide sequence. Amino acids are numbered above the line and number 1 indicates the N-terminal residue. The incomplete signal sequence is underlined by a broken line to residue −1. The two glycosylation sites are marked by stars and the single hydrophobic transmembrane region is underlined by a solid line. Cysteine residues involved in disulphide bonding are circled.

FIG. 12A-B. Homology of the human FcR encoded by HFc3.0 cDNA with the mouse alpha and beta1 FcR. Alignment of the nucleotides of the human FcR with both mouse alpha (A) and beta1 (B) FcR. Amino acid residues common to the human FcR encoded by HFc3.0 and the alpha FcR (A) or beta 1 (B) are shown by asterisks. The human (HFc3.0) mouse alpha or beta FcR leader sequence, extracellular domain, transmembrane domain and cytoplasmic domains are indicated by the sequences between the vertical arrows. The cysteine (C) residues within the extracellular domains (involved in S—S bonds) are identified by the solid circles.

Figure 13:
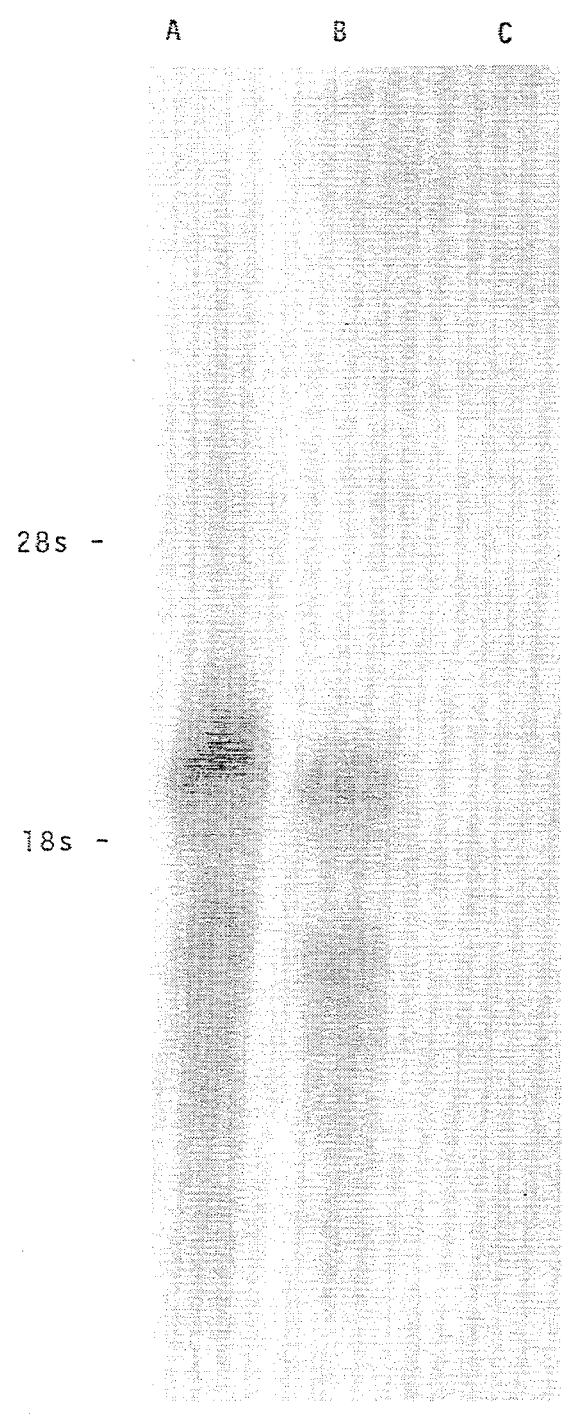

FIG. 13 Northern blot analysis of total RNA isolated from normal human spleen and probed with the cDNA insert from HFc3.1. The 28s and 18s ribosomal RNAs are indicated. A, 20 ug RNA loaded; B, 5 ug RNA loaded; C No RNA.

Figure 14A:
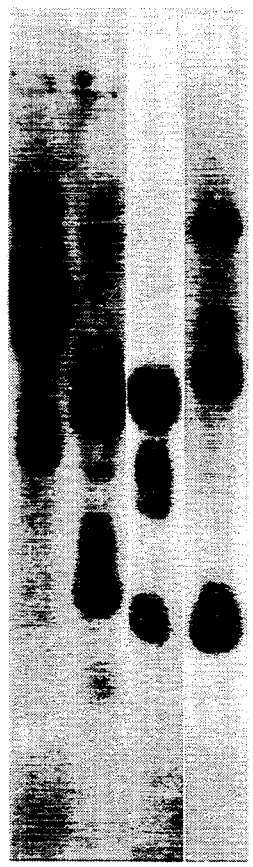
Figure 14B:
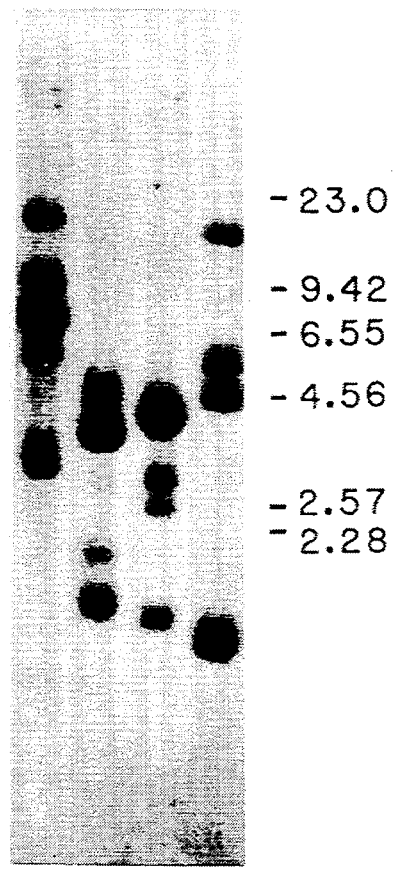

FIGS. 14A-B. Southern blot analysis of the human FcR gene. Human thymus DNA (A) and human peripheral leukocyte DNA (B) was digested with 1, Hind III; 2, PvuII; 3, EcoRI and 4, PstI and probed with the cDNA insert from HFc3.1. Molecular size markers (HindIII digested RNA) are indicated.

Isolation of full length cDNA clone: The Fc(gamma)R has been purified to homogeneity using the anti-Ly-17.2 antibody (FIG. 1). Protein and peptide sequencing studies have enable one third of the molecule to be sequenced (Table 1 ). Consensus oligodeoxynucleotide probes constructed from the protein sequence (Table 2) were used to isolate a cDNA clone (Pfc24). Southern analysis established that the cDNA insert of Pfc24 reacted with the probes (FIG. 2). Maxam-Gilbert sequencing of the 5' and 3' ends of Pfc24 (FIG. 3A, B) indicated it that it was not full length since no entire leader sequence or inframe termination codon was apparent at the 5' and 3' ends respectively. A full length cDNA done, pFc113 (FIG. 3) was isolated by reprobing the WEHI 3B library with oligodeoxynucleotide probes constructed from the nucleotide sequence of the 5' and 3' ends of pFc24. These probes corresponded to nucleotides 140-187 (Probe 1.5) or 959-1000 (probe 1.6) (FIG. 3B, Table 3) and only clones to which both probes hybridised were subsequently isolated. The cDNA insert of pFc113 contains approximately 2.0 kilobase pairs whereas that of pFc24 has only 962bp but is entirely embodied in pFc113 between nucleotides 61 and 1023.

Nucleotide and amino acid sequence: The amino acid sequence predicted from the nucleotide sequence of pFc113 (FIG. 3B) indicates that mature FcR is a membrane molecule composed of 301 amino acids and is synthesised with a 29 amino acid leader sequence. The amino acid sequences of 10 of 11 peptides we had previously sequenced from immunopurified FcR were found encoded by pFc113 cDNA (FIG. 3B, Hibbs et at, 1986). Miscalling of several amino acid residues during sequencing of the peptides accounts for the differences between the sequence of peptides L5 and CNBR and the predicted sequence of these regions from the cDNA clone. Also the CNBR peptide is preceded by a Trp not the predicted Met but it is known that CNBR will cleave on the C terminal side of Trp residues in acid solutions (Ozols et al, 1977).

Several other important observations can be made from the predicted amino acid sequence. Firstly, a single transmembrane region of 28 amino acids extends from Leu180 to the sequence Lys209-Lys210-Lys211 and separates the 94 amino acid long cytoplasmic region from the 179 extracellular amino acids. Secondly, the extracellular portion of the FcR molecule contains two regularly spaced pairs of Cys residues, the first pair Cys 28 and Cys 70 separated from each other by 41 amino acids and the second pair Cys 109 and Cys 153 separated by 43 amino acids. This regular arrangement suggests the extracellular portion may be organised into two disulphide bonded domains (see homologies below). Thirdly, four potential N-linked glycosylation sites are present in the extracellular region of the receptor, with two glycosylation sites located within each of the putative domains. These potential glycosylation sites have been verified as being authentic sites of carbohydrate attachment (Green et al, 1985 and see "Additional Structural Features of murine FcR" below).

Homologies of Murine FcR: Comparison of the amino acid sequences within the FcR molecule (assessed using the Dayoff ALIGN programme, Dayhoff et al, 1983) indicated that there was a significant degree of internal homology within the extracellular domains (FIG. 4A). Using the mutation data matrix, scoring is based on the extent of mutation required for amino acid substitution in established protein families. The score for the optimal alignment is then represented as the number of standard deviations by which the maximum score for the alignment of two sequences exceeds the score for a large number of alignments after randomization of the original sequences (Dayhoff et al, 1983). Arbitrary setting of the boundaries of these domains around the pairs of Cys residues showed that alignment of amino acids 5-86 (FcR, domain 1) with amino acids 88-175 (FcR, domain 2) gave 29% identical residues with an ALIGN score of 7.1 SD i.e. the probability of such an alignment occurring by chance is $>10^8$ and implies the tandem duplication of a single domain. Such repeated domain structures are evident in Ig and related molecules that comprise the Ig superfamily (Williams 1985). To further examine possible homologies to other molecules we undertook computer searches of a number of nucleic acid and protein data bases. These revealed the FcR domain 1 was most homologous to murine Class II antigens in particular to the Ig like beta2 domain of I-Ebeta and gave a highly significant ALIGN score of 8.3SD. In addition to the homology with Class II antigens, other features of the FcR domains indicate their relatedness to Ig superfamily members. The homology to members of the Ig supergene family is seen principally around the Cys residues. The sequences surrounding cysteine residues 70 and 153 were shown to be highly representative of the consensus sequence (Gly-X-Tyr-X-Cys) around the disulphide-bonded Cys residue in IgV-region domains. In addition, the sequences flanking Cys residues 28 and 109 were indicative of the disulphide-bonded Cys near the amino-terminus of the V-region of Ig chains and other Ig related molecules. Furthermore, the Trp residue located 13 residues downstream from Cys 28 and a Phe residue 13 residues downstream from Cys 109 are commonly observed in this position of Ig-like structures. The Ig related molecules Thy-1 and CD4, which also possess these characteristics have been shown experimentally to contain intrachain disulphide bonds (Williams and Gagnon, 1982; Classon et al, 1986a).

It is clear therefore that the receptor for immunoglobulin shows a common evolutionary ancestry with its ligand but comparison of entire Ig and FcR domains shows a low overall homology indicating that they must have diverged relatively early in evolution. The high degree of homology with MHC Class II molecules is interesting in the light of the physical association of some FcR with Class II molecules on the cell surface (Dickler and Sachs, 1974).

In addition to the poly Ig receptor (see above), we also sought homology to other IgG binding molecules. No homology of FcR domains to Staphylococcal protein A (Sjodahl, 1977) was found. The Fc(gamma)R receptor described herein is highly homologous to other beta1 Fc(gamma)R except for a stretch of 9 amino acids in the cytoplasmic tail from Gly241 to Pro249. The discrepancies between the nucleotide/amino acid sequences shown in FIG. 3B may have arisen by the omission of three nucleotides. The nucleotide and predicted amino acid sequence of the beta1 form of the Fc(gamma)R therefore is that shown in FIG. 3B. In addition, another form of the Fc(gamma)R is highly homologous to the FcR described here—almost certainly being a splice variant. The splice site occurs in the region encoding the intracellular domain indicating that the beta1 and beta2 forms of the FcR have identical extracellular domains. A third form of the FcR has also been identified by cDNA cloning studies and designated the alpha FcR. The mature alpha protein shows a little variation from the receptor described herein with approximately 7% variation in amino acid content of the ligand binding domains. All major structural features in the domains of the three variants (alpha, beta1, beta2) are conserved, i.e. (4 N-linked carbohydrate side chains, 2 pairs of cysteine residues). Thus molecular analysis of Fc(gamma)R clearly indicates that murine FcR are a family of highly homologous proteins. It should also be noted that the Ig binding proteins—protein A and the FcR described herein all have repeated ligand binding domains which may be necessary for stability and specificity of ligand binding.

Additional Structural Features of Murine FcR: We have demonstrated that adjacent pairs of cysteine residues in purified Fc(gamma)R are involved in disulphide bonding. Protein was purified by affinity chromatography then digested with proteolytic enzymes either before or after reduction of disulphide bonds with dithiothreitol.

Digests were then fractionated by reversed-phase chromatography. Peptides present in the digests of unreduced Fc(gamma)R but absent from the digested reduced Fc(Gamma)R were sequenced and shown to correspond to disulphide-bonded peptides. The results obtained indicated that Cys 28 is disulphide-bonded to Cys-70 and that Cys-109 and 153 are involved in disulphide bonding.

Extensive peptide sequencing has also determined that four possible N-linked glycosylation sites in mouse Fc(gamma)R are in fact authentic sites of carbohydrate addition. This was judged by the absence of an asparagine in the expected position in the peptide sequence.

Expression of mRNA: Analysis of FcR expression in cell lines was then performed by Northern blotting. Two mRNA transcripts were evident when probing poly-A+ mRNA from the WEHI 3B cell line, with nick translated cDNA (FIG. 5A). These transcripts were absent from the FcR cell line F4N. Since there is FcR heterogeneity with respect to both specificity and expression in cell lineages (Dickler, 1976; Unkless et at, 1981; Teillaud et at, 1985; mRNA from cell lines of different lineages was examined (FIG. 5B) using an oligodeoxynucleotide probe (Probe 1.10) (corresponding to nucleotides 545-574) that hybridised to both transcripts in WEHI 3B cells (FIG. 5B, track a). Northern blots showed that while both transcripts were present in the myelomonocytic cell lines WEHI 3B, the lower Mr species was predominant in J774 macrophage cells (FIGS. 5B, track b) and was completely absent from the FcR+ lymphoma K36, where only the higher Mr species could be detected. The presence of multiple Fc(gamma)R mRNA transcripts (termed alpha, beta1 and beta2, beta1 being identical to that encoded by pFc113 described herein) in different cell types was also noted.

Relationship of mRNA transcripts and surface FcR: To establish the relationship between mRNA transcription and surface Fc(gamma)R expression, we investigated the presence of mRNA transcripts by Northern analysis using oligonucleotide probes specific for the beta1, beta2 and alpha transcripts (Table 3) and compared this with immune complex binding (using rabbit IgG and various IgG isotypes) and whether the cells were Ly-17.2+ or 2.4G2+ at the surface (Table 4).

The results indicate that the beta1 Fc(gamma)R is the receptor for IgG1/2b, hetrologous IgG and possibly other Ig since cells which express only the beta1 receptor only can bind IgG1/IgG2b as well as rabbit IgG coated erythrocytes (Table 4). In addition, K36 cells have the Ly-17.2+ and 2.4G2+ molecules which have been shown to be identical and are epitopes on the Fc(gamma)R molecule (Unkless, 1979; Hibbs et at, 1985; Holmes et al, 1985). Furthermore antibodies to these molecules completely inhibit the binding of IgG1/2b and rabbit IgG complexes to the cell surfaces. Thus the beta1 variant must code for molecules which have Fc binding ability and the epitopes detected by the 2.4G2 and Ly-17.2 antibodies. Both the Ly-17.2 and 2.4G2 epitopes are clearly present on the beta1 and beta2 molecules since both antibodies were used to purify these molecules for amino acid sequencing in this study. Finally, the pFc113 cDNA (in the pKC3 vector) described herein was transfected into FcR negative LTA-5 cells resulting in expression of FcR (Ly-17.2) on the cell surface (Table 4) indicating that this clone encodes an immunoglobulin binding FcR. The interactions of the alpha and beta 2 receptors with antibody and immune complexes remains to be precisely determined. WEHI 3B and J774 cells both express alpha and beta1 mRNA transcripts but only J774 cells express beta2 mRNA although both bind IgG1/2b and rabbit IgG complexes and are Ly-17+ (Table 4). Whilst cDNA expression experiments will be needed to define the specificity of these receptors, it is likely that the alpha, beta1 and beta2, receptors will have the same binding properties of immune complexes.

Southern Blot Analysis: Southern hybridisation studies were performed to determine whether the heterogeneity observed at the mRNA and protein levels was also apparent in the genome (FIG. 6). Probing of murine spleen DNA digested with Hind III or Pst I (FIG. 6, tracks a,c) generated two fragments to which the cDNA hybridised. Digestion with Eco RI (track b) also produced two major and several other weakly hybridised fragments. Thus it appears likely that only a single, or few, copies of a highly conserved gene are present in the genome. The heterogeneity of receptors shown by serological studies, together with the presence of multiple mRNA transcripts indicates the receptors are likely to be a family of homologous proteins. Isolation of Human Fc(gamma)R cDNA Clones:

Since human Fc can bind mouse and human immunoglobulin and have many similarities with mouse FcR, (Dickler, 1976; Anderson and Abraham, 1980, Kulczycki et at, 1981; Perussia et at, 1983; Dorrington and Klein, 1983), it is likely that there is a high degree of structural and functional homology which conserved at the nucleic acid and amino acid levels. Thus we used the mouse cDNA pFc24 and a combination of oligonucleotides, probes 1.5, 1.6, 1.10 (table 3) to screen a library constructed from mRNA isolated from human acute monocytic leukaemia cells THP-1. Several clones were isolated including HFc3.0, HFc3.1 and HFc3.47. The results (FIG. 7) demonstrated that, 1. pFc113 cDNA hybridised to the cDNA inserts of HFc3.1 and HFc3.47; 2. probe 1.5 hybridised to HFc3.1 cDNA but not to HFc3.47; 3. probe 1.10 hybridised weakly to HFc3.1 cDNA but not to HFc3.47; 4. probe alpha did not hybridise to either done and 5. probe 1.6 hybridised to HFc3.47 but not HFc3.1. None of the probes, except probe 1.6, hybridised to the lambda arms—the hybridisation of probe 1.6 to the lambda arms was due to incomplete digestion prior to Southern transfer. The likely homology of the HFc3.1 and HFc3.47 cDNA clones to the mouse cDNA clones was then confirmed by nucleotide sequencing.

Characterisation of Human FcR cDNA: The human cDNA inserts were subcloned into plasmid vectors. The complete nucleotide sequence of a cDNA encoding the human Fc(gamma)R and its predicted amino acid sequence is shown in FIG. 8. Clone HFc3.1 contains sequence encoding the mature Fc(gamma)R protein and most of the leader sequence, as well as the entire coding sequence. The high degree of homology, seen both at the nucleotide and amino acid level, between the mouse FcR sequences and the sequence of HFc 3.1, confirms that this done encodes human FcR. The complete amino acid sequence of the human FcR, aligned with the sequences of mouse alpha and beta1 FcR is shown (FIG. 9A,B). Breaks have been introduced to optimize the alignment. The incomplete leader sequence of the human FcR encoded by HFc 3.1 is highly homologous to the leader sequence of the mouse alpha FcR (56% conservation of amino acids) (FIG. 9A) but bears no homology to the mouse beta1 Fc(gamma)R leader sequence (FIG. 9B). The N-terminus of the human Fc(gamma)R has been predicted on the basis of homology to the mouse alpha Fc(gamma)R N-terminal sequence. The region between the N-terminus and the first cysteine residue is the most highly conserved region between the two species, showing 71 and 73 percent amino acid homology with the murine beta1 and alpha Fc(gamma)R respectively (FIG. 9A,B ). There is also a high level of amino acid conservation in the remaining extracellular portion between FcR of mouse and man. Like the mouse, the extracellular region is divided into two disulphide-bonded domains: the first pair of cysteine residues being separated by 41 amino acids and the second pair by 43 amino acids. Both disulphide bonded domains bear striking homology to the mouse beta1 and alpha Fc(gamma)R. Amino acid sequence comparison of the first domain shows approx. 56 percent conservation between the human FcR and both mouse alpha and beta Fc(gamma)Rs (FIG. 9A,B). Similarly, there is approx. 56 percent conservation of amino acids in the second domain between the human Fc(gamma)R and mouse alpha and beta FcRs. Two potential N-linked glycosylation sites are present in the extracellular region of the human FcR (one in each of the domains) (FIG. 8) and correspond to two of the four sites present in both mouse alpha and beta1 Fc(gamma)Rs (FIG. 3B). The human Fc(gamma)R has a transmembrane region of 28 amino acids extending from residue 219 to the hydrophilic stop transfer sequence Arg (245)-Lys (246)-Lys (247)-Arg (248)(FIG. 8). This transmembrane sequence is highly homologous to the mouse beta1 Fc(gamma)R (50 percent amino acid homology), but shows no homology to the transmembrane sequence of the mouse alpha Fc (gamma) R receptor (FIG. 9A,B).

An in frame termination codon is found at nucleotide 1040 yielding a 75 amino acid intracytoplasmic domain. Comparison of the cytoplasmic domains of both mouse Fc(gamma)Rs with the human Fc(gamma)R shows little identity of either nucleotides or amino acids (FIG. 9A,B).

As well as the very low level of homology obscured between mouse and human Fc(gamma)R cytoplasmic domains, another clear difference between the mouse and human FcR sequences was apparent. The human FcR sequence contained an additional 117 nucleotides which result in an insertion of 39 amino acids between the two extracellular domains (FIG. 8). This sequence is absent from mouse FcRs (FIG. 3B,9A,B) and most likely represents an intron sequence. This is inferred from the sequencing of murine genomic clones.

The striking homology of this human Fc(gamma)R to both alpha and beta1 murine Fc(gamma)Rs in the extracellular domain may reflect the fact that human FcR bind mouse IgG and mouse FcR bind human Ig. The cytoplasmic domain of the human HFc3.1 FcR is totally unique and bears no resemblance to either mouse alpha, beta1 or beta2 intracellular domains. This difference could mean the presence of a homologous product in the mouse which has yet to be detected or may reflect the evolutionary divergence of the human and mouse proteins in a region where there may be a high rate of mutation.

Figures 10A, 10B:
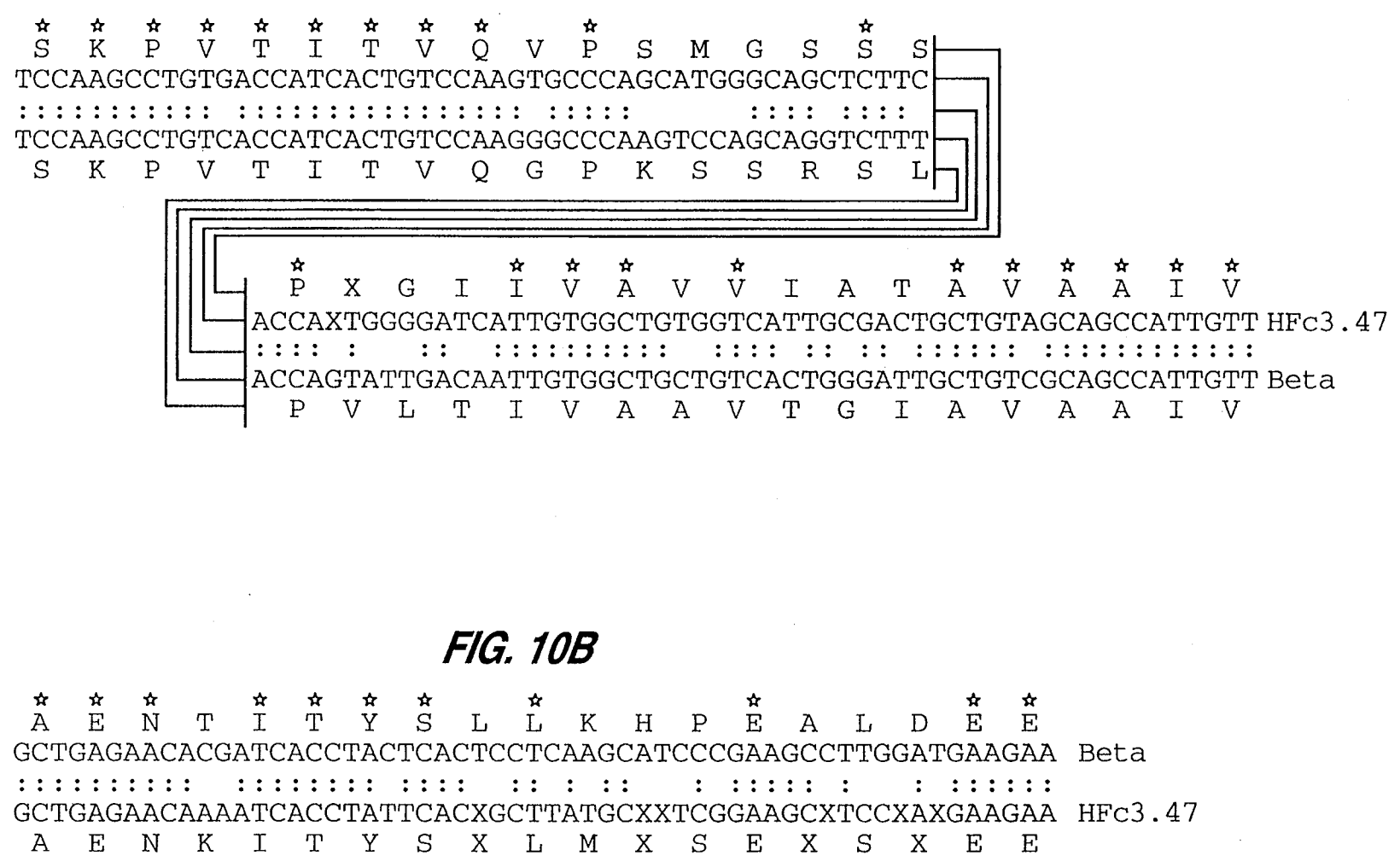

Partial nucleotide sequence of HFc 3.47 has also revealed homology with the mouse FcRs (FIG. 10). Two non-overlapping fragments were sequenced and the first fragment (FIG. 10A) revealed 80% nucleotide homology with the corresponding sequence in beta1 FcR (nucleotides 629-733). This sequence is present in beta2 and a similar sequence in alpha. The second fragment shared 72% nucleic acid homology with nucleotides 959-1015 of the beta1FcR, this sequence also being present in the beta2FcR but not alphaFcR.

An additional variant sequence was also obtained from the THP-1 library HFc 3.0, the sequence of which is shown in FIG. 11. Like HFc 3.1, HFc 3.0 encodes a protein highly homologous to the mouse alpha and beta FcR receptors (FIG. 12A,B). The nucleotide sequence HFc 3.0 is identical to HFc 3.1 with the exception of large segment (nucleotides 338-455 in HFc 3.1 ) between the two disulphide bonded domains which has been deleted in HFc 3.0. The protein encoded by HFc 3.0 has an extracellular ligand binding region consisting of two disulphide bonded domains each with a site of attachment for N-linked carbohydrate. In addition, the encoded protein has a 28 amino acid transmembrane region and 75 amino acid cytoplasmic tail. The extracellular region shows an overall homology of 67% identical amino acid residues and the transmembrane region has 14 of 28 amino acid identities with the mouse beta1 and beta2 transmembrane region (FIG. 12A,B).

Expression of Human FcR mRNA: Northern blots were performed to analyse FcR expression in normal human spleen. Two mRNA transcripts were apparent after probing total mRNA from normal human spleen with the cDNA insert from pHFc 3.1 (FIG. 13). The presence of at least two hybridising mRNA species in human spleen probably indicates that, like the mouse, there are multiple human FcR proteins arising from either one or more genes.

DNA Analysis: Southern analysis of human genomic DNA from thymus and peripheral blood leukocytes (PBL) (FIG. 14)demonstrated that identical restriction fragments were present in thymus and PBL DNA when digested with the same restriction enzyme. This indicates that since thymocytes are mostly FcR− and PBLs mostly FcR+, that the FcR gene is not rearranged. In addition since there were only a few major hybridising restriction fragments it is likely that there is a single or few copies of a highly conserved gene in the human genome. Since human FcR can bind mouse and human immunoglobulin and have many similarities with mouse FcR, (Dickler, 1976; Anderson and Abraham, 1980, Kulczycki et al, 1981; Perussia et al, 1983; Dorrington and Klein, 1983), it is likely that there is a high degree of structural and functional homology which conserved at the nucleic acid and amino acid levels. Thus we used the mouse cDNA pFc24 and a combination of oligonucleotides, probes 1.5, 1.6, 1.10 (Table 3) to screen a library constructed from mRNA isolated from human acute monocytic leukaemia cells THP-1. Several clones were isolated including HFc3.1, 3.0 and 3.47. Southern analysis of EcoRI digested DNA prepared from each of these clones showed that the mouse beta1 cDNA (from pFC24) hybridised to the cDNA insert of each HFc done, i.e. HFc3.0, HFc3.47, HFc3.1. The oligonucleotide probe 1.5 hybridised to the cDNA insert of HFc3.1 and 3.0 and the oligonucleotide probe 1.6 to the cDNA insert of HFc3.47. The cDNA inserts were purified and subcloned into M13mp8 and M13mp9 bacteriophages and sequenced by the dideoxynucleotide method according to the strategy outlined in FIG. 7a. After sequencing, these clones showed homology with the mouse Fc(gamma)R and indeed identify the Fc(gamma)R. This strategy and similar could be used to isolate the Fc(gamma)R of any species.

IMPORTANCE OF DIFFERENT PARTS OF THE SEQUENCE

The amino acid sequence is divided into several parts (FIGS. 3B,8,9,11,12):
Leader sequence
Extracellular Region
Transmembrane Region
Intracellular Region (Cytoplasmic Region)
The Leader Sequence
The leader sequence of 29 amino acids in the beta1 FcR allows translocation of the nascent protein across the endoplasmic reticulum. The key point of this sequence is its hydrophobic nature (required for membrane insertion) and substitution, addition or deletion of one or more hydrophobic (non-polar) amino acids would not substantially alter this function (see list later).
Extracellular Region.
The extracellular region (FCR) consists of 179 amino acids; their function is to act as the receptor for the Fc piece of Ig molecules. This binding site has not yet been identified but comments on the nature of the sequence are relevant. (a) The FcR is divided into two domains by cysteine residues, Domain 1: Cys 28-Cys 70; Domain 2: Cys 109-Cys 153. Both of these domains may have FcR activity as they are highly homologous. Within each domain all or most of the amino acids are likely to be involved in Ig binding as they are conserved—the two domains are conserved in man and mouse. (i) Thus when the murine sequences are compared for internal homology (i.e. domain 1 and domain 2) they are very similar. (ii) Further, when domain 1 of mouse is compared with that of man, each contain 43 amino acids, of these 24 are identical and in the identical position, of the 19 differences 8 are conservative changes in that only 1 nucleotide has been changed, and of the remaining changes, 6 of the 19 are in the same amino acid group (see below) and 13 are in different groups.

Thus the whole sequence in the domain or minor variations thereof are most likely to be involved in Ig binding.

The amino acids substituted belong to the same groups and would therefore not substantially alter the tertiary structure of the molecule and the groupings of amino acids are:

(i) non-polar amino acids A,V,L,I,P,F,M,W.
(ii) basic side chain K,R,H
(iii) acidic side chain E,D
(iv) polar side chain G,N,Q,C,S,T,Y A, ala=alanine; C, cys=cysteine; D, asp=aspartic acid; E, glu=glutamic acid; F, phe=phenylalanine; G, gly=glycine; H, his=histidine; I, ile=isoleucine; K, lys=lysine; M, met=methionine; N, asn=asparagine; P, pro proline, Q, gln=glutamine; R, arg=arginine; S, ser=serine; T, thr=threonine; V, val=valine; W, trp=tryptophan; Y, tyr-tyrosine.

Transmembrane Region.

This consists of 28 amino acids and extends from Leu 180–Lys 209 in mouse beta1 FcR. The key feature of this is the hydrophobic nature of the sequence is required as this portion interacts with the hydrophobic cell membrane and anchors the molecule in the cell membrane. Because of the hydrophobic nature, it follows that minor alterations of sequence - substitution of one non-polar amino acid by another, would not alter the essential function of the transmembrane region. It should be noted that such hydrophobic (non-polar) amino acids are alanine (A); valine (V); leucine (L); isoleucine (I); proline (P); phenylalanine (F); methionine (M) and tryptophan (W).

Intracellular Region.

The intracellular region is involved in signal transmission-obtained when the Fc of Ig binds to the FcR. The mode of signal transmission is unknown. A useful sequence of the FcR is described; it is likely that variations of this sequence, obtained by deletion of parts of the whole sequence, could also function in signal transmission. The region of the beta1 receptor that is spliced out in beta2 is important in cells expressing these molecules.

Variants on the materials the subject of this specification are possible:

A. Sequence Variation

The nucleotide sequences encoding the receptor can be variable:

1. Because of the degeneracy of the genetic code nucleotide change does not necessarily bring about a change in the amino acid encoded, e.g. the codon GUU specifies a valine residue as do the codons GUC, GUA, GUG each being different by a single nucleotide.
2. Two or three nucleotide changes can give rise to the same amino acid, e.g. codons UUA, UUG, CUU, CUC, CUA, CUG all encode Leucine. Codons AGU, UCC, UCU, UCA, UCG encode serine.
3. Changing one or two nucleotides may result in a conservative amino acid change unlikely to greatly affect the function of the protein, e.g. codon UUG specifies leucine and AUU specifies isoleucine. Also UGG specifies tryphophan and UUU specifies phenylalanine—all conservative changes.
4. Allelic variations. Variations in nucleotide sequence and amino acid sequences of the encoded protein as well as resultant may occur between individual members of the same species. These variations arise from changes in the nucleotide sequences encoding the protein. Thus different forms of the same gene (called alleles) give rise to protein of slightly different amino acid sequence but still have the same function.
5. Variation can occur as the result of differential mRNA splicing where one gene composed of many different segments (exons) of coding sequence—DNA encoding the mature protein—gives rise to a RNA that is spliced such that the portion of the RNA derived from certain exons are removed. Selection of exons is different in different cell types, e.g. the beta1 and beta2 forms of FcR or the alpha and alpha' forms of Ly-2.
6. Proteins having the same function, e.g. immunoglobulin binding, may arise from related genes. Many protein gene families have been described, e.g. immunoglobulins which have nucleotide and amino acid sequence variation but retain their primary function of antigen binding. Such homologous proteins are encoded by homologous genes. These genes arise by duplication of one original gene or by gene conversion.
7. Variation may be intentionally introduced by:
   (a) Mutating cloned cDNA or genomic DNA by point mutation, rearrangement or insertion of related or unrelated DNA into the cDNA or genomic clones encoding the functional protein. Such mutated (variant) clones can be used to generate variant proteins or peptides which in the context of this specification may have Ig binding function.
   (b) By enzymatic cleavage of the protein (from either in vitro synthesis or normal cell synthesised protein) with or without repair/rearrangement of the cleavage products.
   (c) By chemical modification.
   (d) By irradiation.

B. Use of portions of the FcR protein.

The present invention also includes the use of segments of the FcR protein (peptides) and variant peptides synthesised or genetically engineered that have the capacity to bind Ig. The FcR protein and its variants extend from the first methionine in the leader sequence to the most C terminal amino acid of the protein.

C. Isolation of other FcR.

Other FcR within and between species that are homologous at the nucleic acid, protein and functional levels. Because of substantial sequence homologies, the cDNA clones described herein would enable the isolation of related sequences encoding FcR from man, the mouse and other species.

The Principal Novelty of the Invention includes but is not limited to:

(i) Description of a molecule, the FOP, which has the capacity to bind the Fc piece of Ig. (ii) The structural arrangement of the 2 extracellular domains which show homology to each other in both man and mouse. (iii) The similarity of these domains in man and mouse. (iv) Differences in the intracellular regions in man and mouse; indicating that signals can be transmitted by different structures. (v) cDNA and other DNA and RNA material encoding for the receptor. (vi) Various vectors including materials.

TABLE 1-continued

The N-terminal sequence of the Fc receptor and amino acid sequences of Fc receptor peptides

| Peptide | Sequence |
| --- | --- |
| V17 | THDLPKAVVKLEPPWIQV |
| CNBr-I | MRNKHLNRIVFL(Q/T)N(Y)(K) |

"-" indicates an unassigned residue
() indicates an uncertain assignment

TABLE 2

Amino acid Sequences of lysine-C peptides of the murine Fc receptor and corresponding nucleotide sequence of oligonucleotide probes. Oligonucleotide probes were constructed on the basis of codon usage frequencies and synthesised to be complementary to mRNA.

L3  (Lys)-Gly-Ser-Leu-Gly-Arg-Thr-Leu-His-Gln-Ser-Lys
Probe 1 3' UUC-CCU-AGG-GAC-CCU-UCU-UGG-GAC-GUG-GUC-AGG-UUC 5'
L4  (Lys)-Pro-Val-Thr-Ile-Thr-Val-Gln-Gly-Pro-Lys
Probe 3 3' UUC-GGU-GAC-UGG-UAG-UGG-GAC-CUC-CUU-GGU-UUC 5'
L5  (Lys)-Ser-Val-Arg-Tyr-Gly-Gly-Tyr-Ser-Ser-Ser-Phe-Cys-Ile-Pro-Lys
Probe 23'UUC-AGG-CAC-USU-AUG-CCU-CCU-AUG-AGG-AGG-AGG-AAG-ACG-UAG-GGU-UUC 5'

TABLE 3

Oligodeoxynucleotide probes used in this study

| Name | Sequence* | Corresponding sequence in pFc113 cDNA |
| --- | --- | --- |
| Probe 1.5 | 5' ACGGGGGCTCGAGTTTGACCACAGCCTTTGGAAGATCATGAGTCCCAG3' | 135–182** |
| Probe 1.6 | 5' TTCGGGATGCTTGAGGAGTGAGTAGGTGATCGTGTTCTCAGCCTC3' | 956–1000** |
| Probe 1.10 | 5' GTGGTTGGCTTTGGGGATAGAGAAATTACT3' | 545–574** |
| Probe alpha | 5' AGGGAGAAAGCAGTGTGGTACCAGAC3' | — |
| Probe beta1 | 5' CTGTCTGTACTCACCTACTTCCTCTGGAAG | 821–850**, |
| Probe beta2 | 5' AGGAGGATTGTCTGGAACCTGCTT3' | — |

*Sequences complementary to mRNA
**Sequences from this paper and Hibbs et al 1986

TABLE 4

Comparison of Immune Complex Binding and FcR mRNA synthesis

| Cell Line (Type) | FcR mRNA* variant | % EA rosettes** gamma1/ gamma2b | Rabbit Ig | % Ly-17+ cells ° |
| --- | --- | --- | --- | --- |
| K36 (T lymphoma) | beta1 | >99 | >99 | >99 |
| NEHI 3B (myelomonocytic) | alpha, beta1 | >99 | >99 | >99 |
| J774 (macrophage) | alpha, beta1, beta2 | >99 | >99 | >99 |
| Transfectants+ | NT | NT | NT | 70 |

*alpha, beta1, beta2 mRNA transcripts detected by Northern analysis using specific oligonucleotide probes (Table 1).
**% EA rosetting cells detected using IgG2b monoclonal anti-TNP antibodies or rabbit IgG anti sheep erythrocytes (see Materials and Methods). °determined by sheep anti-mouse Ig rosetting with anti-Ly-17.2 monoclonal antibody. Background levels of rosette formation were determined using an irrelevant antibody and were <5%. These cells are also tested with 2.4G2 antibody and show identical reactions to the Ly-17.2 antibody.
NT = not tested
+ The Pst-1 fragment of the pFc113 cDNA insert was subcloned into pKC3 and transfected into LTA-5 cells using the CaCl$_2$ method.

TABLE 1

The N-terminal sequence of the Fc receptor and amino acid sequences of Fc receptor peptides

| Peptide | Sequence |
| --- | --- |
| NH2-terminal | THDLPKAVVKLEPP |
| L3 | KGSLGRTLHQSK |
| L4 | KPVTITVQGPK |
| L5 | KSVRHHYSS-FSIPK |
| L9 | KAVVKLEPPWIQLVK |
| V4 | ELSTTGGNSG(S)P(V)(K)N |
| V8 | EQTRLSDPVDLGVI |
| V10 | ENTITYSLLKHPE |
| V11 | EAENTITYSLLKHPE |
| V16 | THDLPKAVVKLEP--IQV |

REFERENCES

Appella, E. Proc. Natl. Acad. Sci. USA 68: 590–594, 1971.

Anderson, C. L. and Abraham, G. N. J. Immunol. 125: 2735–2741, 1980.

Capron, M., Speigelberg, H. L., Prin, L., Bennich, H., Butterworth, A. E., Pierce, R. J., Quassi, M. A. and Capron, A. J. Immun, 132: 462–468, 1984.

Classon, B. J., Tsagaratos, J., McKenzie, I. F. C. and Walker, I. W. Proc. Natl. Acad. Sci. USA 83: 4499–4503, 1986a.

Classon, B. J., Tsagaratos, J., Kirszbaum, L., Maddox, J., Mackay, C. R., Brandon, M. R., McKenzie, I. F. C., and Walker, I. D. Immunogenetics 23: 129–132, 1986b. Dayhoff, M. O., Barker, W. C., and Hunt, L. T. Methods in Enzymol. 91; 524–545, 1983.

Dickler, H. B. Adv. Immun. 24: 167–215, 1976.

Dickler, H. B. and Sachs, D. H. J. Exp. Med. 140: 779–796, 1974.

Dorrington, K. and Klein, M. In Froese, H. and Paraskeva, F. (Eds). Receptors and Ligands in Intracellular Communications, Vol. 2. Structure and Function of Fc receptors, Marcel Dekker, New York, 1983 pp . . . .

Engelhard, M. and Hilschmann, N. Hoppe-Seyler's Z. Physiol. Chem, 356: 1413–1444, 1975.

Fridman, W. H., Rabourdin-Combe, C., Neauport-Santes, C., and Gisler, R. Immun. Rev. 56: 51–88, 1981.

Gough, N. M., Metcalf, D., Gough, J., Grail, D. and Dunn, A. EMBO Journal 4, 645–653, 1985.

Green, G. A., Plutner, H. and Mellman, I. J. Biol. Chem. 260: 9867–9874, 1985.

Hamperly, J. J., Murray, B. A., Edelman, G. M. and Cunningham, B. Proc. Natl. Acad. Sci. USA 83: 3037–3041, 1986.

Hibbs, M. L., Hogarth, P. M. and McKenzie, I. F. C. Immunogenetics 22: 335–348, 1985.

Hibbs, M. L., Walker, I. D., Kirszbaum, L., Chambers, G. W., Pietersz, G. A., Deacon, N. J., McKenzie, I. F. C. and Hogarth, P. M. Proc. Natl. Acad. Sci. USA. 83: 6980–6984, 1986.

Holmes, K. L., Palfree, R. G. E., Hammerling, U. and Morse, H. C. Proc. Natl. Acad. Sci. USA 82: 7706–7710, 1985.

Hogarth, P. M., Edwards J. McKenzie I. F. C., Soding J. N. and Liew F. J. (1982) J. Immunol 46 135–144.

Hubscher, T. and Eisen, A. H. Int. Arch. Allergy Appl. Immun. 41:689–699, 1971.

Humes, J. L., Binger, S., Galavage, M., Kuehl. F. A. Wightman, P. D., Dahlgren, M. E., Davies, P. and Bonney, R. I. J. Immun. 124: 2110–2127, 1980.

Hunkapillar M. W., Hewick R. M., Dreyer W. J. 9 Hoodle (1983) Methods Enzymol 91, 399–413.

Kolsch, E., Haubeck H. and Schuler, W. In Froesse, A. and Paraskevas, F. (Eds) Receptors and Ligands in Intercellular Communication, Vol. 2. Structure and Function of Fc Receptors, Marcel Dekker, New York, 1983, pp 215–231, 1983.

Kulczyeki, A., Solanki, L. and Cohen, L. J. Clin. Invest. 68: 1558–1564, 1981.

Kurlander, R. J., Ellison, D. M. and Hall, J. J. Immun. 133: 855–862, 1984.

Leslie, R. G. Q. Eur. J. Immun. 10: 323–346, 1980.

Lopez, A. F. Strath, M. and Sanderson, C. J. Immunology 48: 503–509. 1983.

Maniatis, T., Fritsch, E. F. and Cambrook, J. in Molecular Cloning, A Laboratory Manual, Cold Spring Harbor Laboratory, New York, 1982.

Mantorani, B. J. Immun. 115: 15–17 (1975).

Maxam, A. M. and Gilbert, W. Methods in Enzymol. 65: 499–560 (1980).

Mostov, K. E., Friedlander, M. and Blobel, G. Nature 308:37–43 (1984).

Nishioka, Y. and Leder, P. J. Biol. Chem, 255: 3691–3694 (1980).

Novotny, J. and Margolies, N. M. Biochem. 22. 1153–1158 (1983).

Ozols, J., Gerard, C. and Stachelek, C. J. Biol. Chem. 252: 5986–5989 (1977).

Parish, C. R. and Haywood, J. A. Proc. Roy. Soc. lond. (Biol.) 187: 47–63 (1974).

Parish, C. R. and McKenzie, I. F. C. J. Immunol. Methods 20: 173–183 (1978).

Perussia, B., Starr, S., Abraham, S., Fanning, V. and Trincheri, G. J. Immunol. 130: 2142–2148 (1983).

Sanger, F., Nicklen, S. and Coulson, A. R. Proc. Natl. Acad. Sci. USA 74: 5463–5467 (1977).

Sjodahl, J. Eur. J. Biochem. 78: 471–490 (1977).

Speigelberg, H. L. Adv. Immun. 35: 61–88 (1985).

Teillaud, J., Diamond, B., Pollock, R. R., Fajtova, V. and Scharff, M. D. J. Immun. 134: 1774–1779 (1985).

Tourvieille, B., Gorman, S. D., Field, E. H., Hunkapiller, T. and Parnes, J. R. Science 234: 610–614 (1986).

Tsay, D. D., Ogden, D. and Schlamowitz, M. J. Immun. 124: 1562–1567 (1980) Unkless, J. C. J. Exp. Meal. 150: 580–596 (1979).

Unkless, J. L., Fleit, H. and Melman, I. S. Adv. Immun. 31:47–270 (1981).

Winnacker, E. L. and Dorper, T. In Gassen, H. G. and Lang, A. (Eds) Chemical and Enzymatic Synthesis of Gene Fragments: A Laboratory Manual, Verlag Cherrie Weinhein, 1982, pp97–102.

Williams, A. F. Nature 314: 579–580 (1985).

Williams, A. F. and Gagnon, J. Science 216: 696–703 (1982).

Yodoi, J. and Ishizaka, K. J. Immun. 124: 1322–1329 (1980).

A deposit of the material referred to herein as pFc24, pFc113 (ATCC 67414), HFc3.0, HFc3.1 (ATCC 67415) and HFc 3.47 (ATCC 67416) was made with ATCC 12301 Parklawn Drive, Rockville, Md. 20852 on or about 29th May, 1987 and with Dr. George Hodges of the Cancer Institute (also known as the Peter McCallum Clinic) of 481 Little Lonsdale Street, Melbourne, Victoria, Australia under terms and conditions permitting access to members of the public.

The claims defining the invention are as follows:

1. An isolated polynucleotide encoding a human Fc receptor for immunoglobulin G comprising nucleotides 83 through 924 of FIG. 11.

2. An isolated polynucleotide encoding a human Fc receptor for immunoglobulin G comprising nucleotides 83 through 601 of FIG. 11.

* * * * *